United States Patent [19]
Kibblewhite et al.

[11] Patent Number: 6,009,759
[45] Date of Patent: Jan. 4, 2000

[54] MINIMIZING THE EFFECT OF BENDING ON ULTRASONIC MEASUREMENTS IN A LOAD-BEARING MEMBER

[75] Inventors: Ian E. Kibblewhite, Strafford; Christopher J. Vecchio, Broomall, both of Pa.

[73] Assignee: Ultrafast, Inc., Malvern, Pa.

[21] Appl. No.: 08/850,139

[22] Filed: May 2, 1997

Related U.S. Application Data

[60] Provisional application No. 60/016,563, May 3, 1996.

[51] Int. Cl.⁷ ..................................................... F16B 31/02
[52] U.S. Cl. .................................. 73/761; 73/597; 73/599
[58] Field of Search ............................. 73/761, 597, 599, 73/627, 629

[56] References Cited

U.S. PATENT DOCUMENTS

| | | | |
|---|---|---|---|
| 3,799,108 | 3/1974 | Mosow | 73/76 |
| 3,822,587 | 7/1974 | Makino et al. | |
| 3,918,294 | 11/1975 | Makino et al. | |
| 4,114,428 | 9/1978 | Popenoe | 73/761 |
| 4,294,122 | 10/1981 | Couchman | |
| 4,428,240 | 1/1984 | Schoeps | 73/761 |
| 4,471,657 | 9/1984 | Voris et al. | |
| 4,569,229 | 2/1985 | de Halleux | |
| 4,601,207 | 7/1986 | Steblay | |
| 4,602,511 | 7/1986 | Holt | |
| 4,846,001 | 7/1989 | Kibblewhite | |
| 5,029,480 | 7/1991 | Kibblewhite | |
| 5,131,276 | 7/1992 | Kibblewhite | |
| 5,156,050 | 10/1992 | Schmid et al. | |
| 5,499,540 | 3/1996 | Whaley et al. | |

FOREIGN PATENT DOCUMENTS

WO 95/22009    8/1995    WIPO .

OTHER PUBLICATIONS

International Search Report dated Sep. 1, 1997.
Junker, Gerard H., "New criteria for self–loosening of fasteners under vibration," Paper presented at the Unbrako Symposium, Olympia, London, Oct. 8, 1969.
Bickford, John A., "An introduction to the design and behavior of bolted joints," Chapter 2, pp. 10–20; Chapter 11, pp. 298–346, Marcel Dekker, Inc., New York, 1990.
Pierce, Allan D., "Acoustics, an introduction to its physical principles and applications,", pp. 370–388, McGraw–Hill, Inc., Woodbury, New York, 1989.
Bobrenko et al., "Ultrasonic Method of Measuring Stress in Parts of Threaded Joins," All Union Scientific Research Institute of Non–Destructive Testing, Kishinev, Translated from Defektoskpiya, No. 1, pp. 59–66, (Jan.–Feb. 1974).

(List continued on next page.)

*Primary Examiner*—Michael Brock
*Assistant Examiner*—Nashmiya Fayyaz
*Attorney, Agent, or Firm*—Ratner & Prestia

[57] ABSTRACT

A load-indicating device including a load-bearing member adapted to deform when stressed. Ultrasonic waves are directed into one end of the load-bearing member and ultrasonic echoes are received at the same end by ultrasonic wave transmitting and receiving equipment. In one embodiment, ultrasonic waves are transmitted and received using an ultrasonic transducer disposed on either the head or the opposite end of the load-bearing member. The head, the end, the shank or a combination thereof are contoured to reduce the influence of geometric variations and asymmetrical stress in the load-bearing member on the ultrasonic measurement. A method is also provided, which encompasses a model, by which preferred geometries of the contoured surfaces of the load-bearing member can be designed. Also provided are a method of making a load-bearing member including contouring at least one end of a load-bearing member, or the shank to reduce the influence of geometric variations and asymmetrical stress in the load-bearing member on ultrasonic measurement, and a method of identifying a contour on a load-bearing member that will provide accurate and reliable ultrasonic load measurements.

21 Claims, 19 Drawing Sheets

OTHER PUBLICATIONS

Johnson et al., "An Ultrasonic Method for Determining Axial Stress in Bolts," A Journal of Testing and Evaluation, vol. 14, No. 5, pp. 253–259 (Sep. 1986).

G.C. Johnson, "On the Applicability of Acoustoelasticity for Residual Stress Determination," Journal of Applied Mechanics, vol. 48, No. 4, pp. 791–795 (1981).

J.S. Heyman and E.J. Chern, "Ultrasonic Measurement of Axial Stress," Journal of Testing Evaluation, vol. 10, No. 5, pp. 202–211 (Sep. 1992).

Gordon, Jr., B.E., "Measurement of Applied and Residual Stresses Using an Ultrasonic Instrumentation System," ISA Transactions, vol. 19, No. 2, pp. 33–42 (1980).

International Search Report dated Dec. 3, 1997.

TENSILE STRESS

TENSION

COMPR.

MINIMIZING THE EFFECT OF BENDING ON ULTRASONIC MEASUREMENTS IN A LOAD-BEARING MEMBER

This application is a continuation of provisional Application No. 60/016,563 filed May 3, 1996.

FIELD OF THE INVENTION

This invention relates generally to load measurement and control in fasteners during assembly and inspection and, more specifically, to a fastener design, and to a method for optimizing that design, which reduces the influence of asymmetrical (non-tensile or "bending") stresses on the reliability and accuracy of ultrasonic tensile load measurements.

BACKGROUND OF THE INVENTION

There are many methods and devices which use ultrasonic waves to measure the tensile load on a load-bearing-member (such as a fastener). Specifically, ultrasonic techniques can be used to provide a precise measure of the tensile load in a fastener (such as a bolt) during its installation or subsequently for purposes of inspection. These techniques are well documented in the prior art. In addition, techniques have been documented which use ultrasonic waves to detect flaws and for other nondestructive evaluation purposes in fasteners and other load-bearing members. The success of all of these techniques depends upon reliably detecting echo signals from within the parts under evaluation.

Several patents have described the use of a pulse-echo technique to measure the stress in a load-bearing member. U.S. Pat. No. 4,294,122 (issued to Couchman) discloses a fastener having an acoustic transducer built into its head or threaded end. The acoustic transducer is used to obtain pre-loading measurements and to provide improved quality control inspection of fasteners. A power-driven wrench incorporating a spring-loaded electrical connection to the transducer is electrically connected to a pulse-echo measuring system. The '122 patent also discloses a pulse-echo technique for measuring pre-load stress. The method includes measuring the time for two sets of echoes to travel the length of the fastener, one set before pre-load and the other set as torque is applied to the fastener. Then, by knowing the material constant M, the grip length $\delta$, the diameter D, an empirical parameter which corrects for stress distribution in fasteners $\alpha$, and the time difference in the travel time of the echoes $\Delta T$, the stress S can be measured to obtain an accurate measure of fastener pre-load by using the following formula: $S=(M/(\delta+\alpha D))\times\Delta T$.

Another patent disclosing the pulse-echo time measurement technique is U.S. Pat. No. 4,471,657 (issued to Voris et al.). The '657 patent discloses an apparatus and method for measuring the length of and stress in a tensile load member. The method includes measuring the time it takes two signals having the same frequency but a pre-determined phase difference to travel the length of a load-bearing member; detecting the longer of the travel times; compensating for the phase difference; and using an intelligent processing and control means to receive the time interval data and process the data to produce an accurate conversion to the change in fastener length or the stress applied to the load-bearing member. The apparatus includes an ultrasonic transducer permanently or temporarily in contact with the load-bearing member.

U.S. Pat. No. 4,602,511 (issued to Holt) teaches a method using the time-of-flight of both longitudinal and transverse waves to determine the stress in a load-bearing member. The '511 patent does not require an ultrasonic measurement to be taken when the load-bearing member is under zero stress. Rather, Holt provides a formula for stress calculation which is independent of the length of the fastener and, therefore, can be used to measure tensile stress in a fastener already under tension. The preferred embodiment uses phase detection for time-of-flight measurement. About 20–100 cycles of 5–10 MHz are transmitted, the transmitted and reflected signals are summed, and the frequency is adjusted for 180° out-of-phase destructive interference or null. Holt also mentions previously disclosed time-of-flight measurement techniques as alternatives.

U.S. Pat. No. 3,918,294 (issued to Makino et al.) describes a method of measuring axial stresses in a bolt. An ultrasonic wave is applied to the bolt to generate forced oscillations and two different natural frequencies are measured in the bolt, one of which is measured when the bolt is under little or no axial force, the second of which is measured when the bolt is under axial stress. The ratio of change or the differential between the first and second frequencies is obtained and is compared to calibration data for the axial stress verses the ratio of change or differential.

Ultrasonic load measurement is a precise measurement technique for determining load in bolted joints. Pulse-echo techniques with removable ultrasonic transducers have been used in laboratories and for quality control for over thirty years. Historically, however, the practical difficulties in achieving reliable acoustic coupling and in incorporating transducers in tool drives have prevented this technique from becoming a general assembly tightening strategy. U.S. Pat. No. 4,846,001 (issued to Kibblewhite) teaches the use of a thin piezoelectric polymer film which is permanently, mechanically, and acoustically coupled to the upper surface of a member and is used to determine the length, tensile load, stress, or other tensile load-dependent characteristic of the member by ultrasonic techniques. Although the invention represented a significant advance over the prior state of the art in terms of performance, ease of manufacture, and manufacturing cost, there are disadvantages with a transducer of this construction. These disadvantages relate to environmental performance, in particular the maximum temperature limitations of the polymer material which restricts its application, and the possibility of the transducer, fixed to the fastener with adhesive, coming loose and causing an obstruction in or damage to a critical assembly.

These disadvantages were overcome by permanent transducer technology developed at Ultrafast, Inc. and disclosed, specifically, in U.S. Pat. No. 5,131,276 issued to Kibblewhite and assigned to Ultrafast, Inc. The '276 patent teaches a load-indicating member having an ultrasonic transducer, including an acoustoelectric film, grown directly on the fastener surface. By growing the acoustoelectric film directly on the fastener, the film is mechanically, electrically, and acoustically interconnected to the surface. This advance not only allows the precise pulse-echo load measurement technique to be used in production assembly but also significantly improves accuracies by eliminating errors that result from axial and radial movement of the removable transducer relative to the bolt and from variations in the coupling media.

With these errors eliminated, the greatest source of inaccuracy in ultrasonic load measurement is bending. Bending stresses in bolts can be caused by one or both of: (1) the "straightening" during tightening of a bolt that has a slight bend as a result of the forming or heat treatment manufacturing process, and (2) the tightening of a bolt in a joint in which the joint bearing surfaces are not parallel. When an ultrasonic wave or beam propagates through a fastener or other load-bearing member in the presence of stresses which are asymmetrical with respect to the axis of propagation, the beam is redirected due to both geometrical aberrations and the effects of material stress on sound velocity. In this situation, the amplitude, phase, and time-of-flight of the received ultrasonic echoes may vary and the measurements based upon them may be adversely affected. Thus, the prior art methods and devices are susceptible in terms of reliability and accuracy to bending stresses induced in a fastener during tightening and normal operation.

U.S. Pat. No. 5,029,480 (issued to Kibblewhite) discloses a load-indicating member (e.g., a fastener) with a shank having at least one external groove. An ultrasonic transducer (preferably a piezoelectric film transducer) is coupled to the load-indicating member so that an ultrasonic wave is directed to the groove. Thus, the groove acts as an artificial reflector by providing a face for reflecting the ultrasonic wave, generated by the transducer, back to the transducer. The head surface of the bolt may be fashioned to direct the acoustic signal toward the artificial reflector.

Although the prior art has discussed the use of radiused or focused surfaces to direct acoustic beams to specific reflecting surfaces (as in the case of artificial reflectors), no use of geometric end or head-shaping to correct for the effects of fastener bending on received echoes has been considered. U.S. Pat. No. 4,569,229 (issued to de Halleux) teaches a method for measuring stresses in load-bearing members which eliminates the need to calibrate for grip length. The method measures the time an echo travels from the top of a load-bearing member to an artificial reflector and back. The artificial reflector constitutes axial, radial, or both axial and radial bore holes or perforations in the load-bearing member. The transit time in the bolt depends on the stress in the bolt.

To overcome the shortcomings of prior fastener designs (particularly with respect to bending), a new fastener design is provided. Also provided is a method for determining that design. The central object of the present invention is to provide a method of making more accurate and reliable ultrasonic measurements in a load-bearing member by reducing the influence of geometric variations and asymmetrical stress in the member. A related object is to provide, through the use of the method of the present invention, fasteners that provide ultrasonic echoes which are significantly more robust in the presence of bending stresses.

SUMMARY OF THE INVENTION

To achieve these and other objects, and in view of its purposes, the present invention provides a load-indicating device comprising a load-bearing member adapted to deform when stressed. Ultrasonic waves are directed into one end of the load-bearing member and ultrasonic echoes are received at the same end by ultrasonic wave transmitting and receiving equipment. In one embodiment, ultrasonic waves are directed through the load-bearing member with a transducer disposed on either the head or the opposite end of the load-bearing member. A portion of the head, the end, a shank or a combination thereof, are shaped or contoured to reduce the influence of geometric variations and asymmetrical stress in the load-bearing member on the ultrasonic measurement. In one embodiment, one or both ends of the load-bearing member is contoured into an approximately spherical shape. In another embodiment, the shank of the fastener is contoured with one or more annular rings forming reflectors for reflecting an ultrasonic echo to a conical groove in the head of the fastener.

Methods are also provided, which encompass a models, by which the preferred geometries of the contoured surfaces of a load-bearing member can be identified and designed. Also provided is a method of making a load-bearing member including contouring at least one end of a load-bearing member to reduce the influence of geometric variations and asymmetrical stress in the load-bearing member on ultrasonic measurement.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Before the introduction of the permanent transducer technology developed at Ultrafast, Inc. and disclosed, specifically, in the '276 patent discussed above, a fastener (e.g., a bolt) was designed solely for its clamping function. A load-indicating member with an acoustoelectric film grown directly on the fastener, however, allows the member to act as both a clamping device and a load sensor. By incorporating minor design changes that affect neither the clamping function of the fastener nor its manufacturing cost, significant improvements in load measurement accuracies are possible—particularly under adverse application conditions which result in severe fastener bending stresses.

Provided immediately below is an analysis of the effects of bending stresses on ultrasonic load measurements. Thereafter, the subject invention is described: a model which was developed to optimize fastener end surface geometry. Bending tests have confirmed that fastener designs determined with the model of the present invention significantly improve load measurement performance under bending, with less than 2% full scale load error resulting from 2° bending in the joint.

Bolt Bending

Bolt manufacturing specifications usually allow for up to 1° of error in the perpendicularity between the under-head and the shank of a bolt but, in practice, except for long bolts, 0.2° to 0.5° is typical. The most severe bolt bending situations usually occur with unmachined cast joint bearing surfaces. The prior art is susceptible in terms of reliability and accuracy to the bending stresses induced in a fastener during tightening and normal operation. The prior art does not disclose any method to preserve the integrity of the amplitude and phase of an ultrasonic echo received from within a fastener in the presence of asymmetrical (bending) stress.

Figure 1:
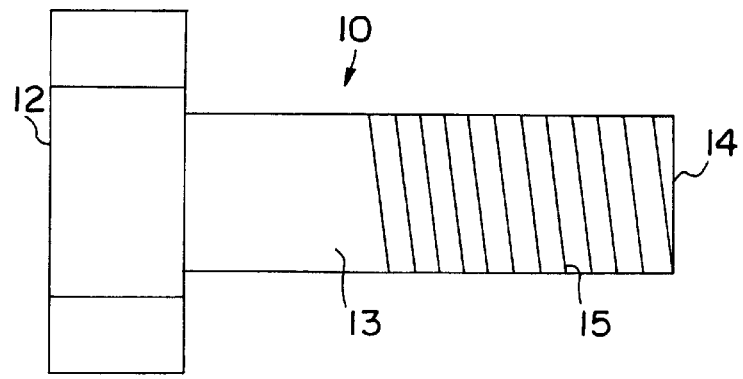
FIG. 1 is a typical threaded fastener having an approximately flat head end surface (head) and a flat threaded end surface (end)
Figure 2:
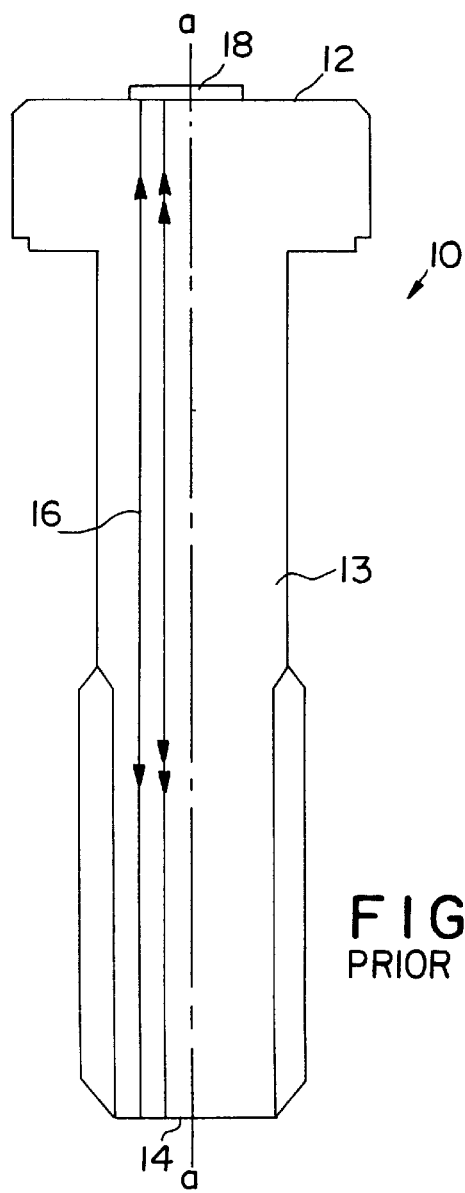
FIG. 2 illustrates the path of an ultrasonic wave in the fastener shown in FIG. 1 when the fastener is not subject to bending.

Shown in FIG. 1 is a typical fastener 10 having a flat head 12, a flat end 14, and an intermediate shank 13. Shank 13 may have threads 15 along all or part of its length. Fastener 10 may be, for example a load bearing member such as a bolt, a stud, or a rivet. With prior art fastener designs for use with ultrasonic load measurement technology, the ultrasonic wave 16 produced by an ultrasonic transducer 18 is reflected from a single reflective surface (e.g., end 14) directly back to ultrasonic transducer 18—as shown in FIG. 2. As discussed more fully below, one skilled in the art will understand that ultrasonic waves may be transmitted through a fastener, and ultrasonic echoes may be received by any conventional means including piezoelectric and electromagnetic transducers, and lasers. The part of the wavefront generated from one side of transducer 18 returns along the same path given a flat parallel reflective surface. In FIG. 2, ultrasonic wave 16 is shown parallel to the central longitudinal axis, a, of fastener 10.

Figure 3:
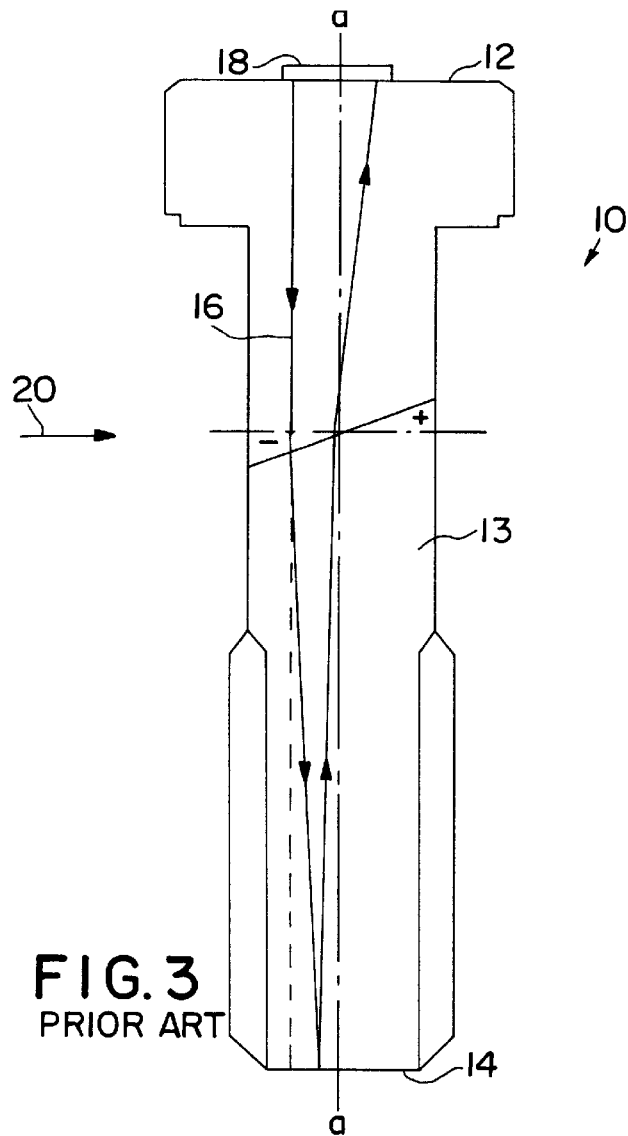
FIG. 3 illustrates the path of an ultrasonic wave in the fastener shown in FIG. 1 when the fastener is subject to bending.

FIG. 3 illustrates fastener 10 subjected to a bending force in the direction of arrow 20. The bending force creates an area of reduced tensile stress (indicated by the minus sign) on the left-hand side of fastener 10 and an area of increased tensile stress (indicated by the plus sign) on the right-hand side of fastener 10. When fastener 10 is subjected to bending stresses, an asymmetric radial stress gradient causes different parts of ultrasonic wave front 16 to propagate at different speeds. Specifically, ultrasonic wave 16 travels faster in the area of reduced tensile stress and slower in the area of increased tensile stress. This causes a deflection (refraction) in the direction of propagation (relative to longitudinal axis, a) and phase differences when ultrasonic wave 16 is received at ultrasonic transducer 18. Consequently, the measurement by ultrasonic transducer 18 of the load in fastener 10 may be inaccurate. An object of the present invention is to direct ultrasonic wave 16 so that the effects of deflection and phase differences are minimized, therefore minimizing the effects of bending.

Figure 4:
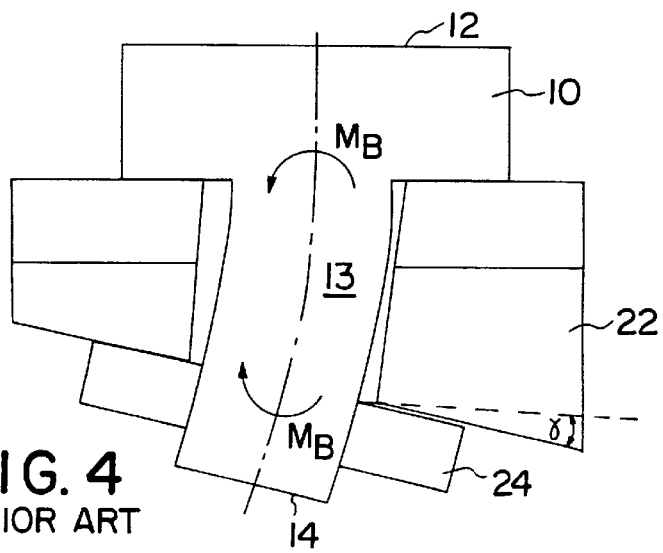
FIG. 4 shows a bolt subjected to bending from non-parallel joint surfaces.

The major cause of bending stresses in a bolt installed into a joint is joint bearing surfaces which are not parallel or not perpendicular to the axis of a tapped hole (see FIG. 4, which illustrates a joint bending angle, γ). For experimental purposes, this situation can be reproduced in a laboratory by introducing angled washers 22 in an instrumented joint. In order for the bolt to be subjected to the maximum effect of angled washers 22, the joint bearing surfaces must be hard, to minimize embedding, and the joint, including the load cell, must be rigid. (An Ultrafast® Certified Test Joint, incorporating a load cell with a specified high bending rigidity, was used to conduct tests.)

In general, when a bolt is tightened in a joint where the bearing surfaces are not parallel, bolt head 12 (or nut 24, whichever is being tightened) moves freely in the radial direction without any significant restraining forces. The joint clearance holes are normally specified to accommodate such variations in joint tolerances. Also, the rotation of head 12 or nut 24 results in motion of the bearing surfaces perpendicular to the radial restraining friction forces and this motion essentially reduces these friction forces to zero. (This phenomena is almost identical to what occurs in vibration loosening of fasteners and is described in detail in G. Junker, "New criteria for self-loosening of fasteners under vibration," 23 pages, Paper presented at the Unbrako Symposium, Olympia, London, Oct. 8, 1969). Consequently, for analysis purposes, the effect of non-parallel joint bearing surfaces, simulated with angled washers 22, can be approximated by pure bending moments, M$_B$, at the joint bearing surfaces with the portion of the bolt shank between these two surfaces subject to a constant bending moment as shown in FIG. 4.

Bolt Model

Figure 6:
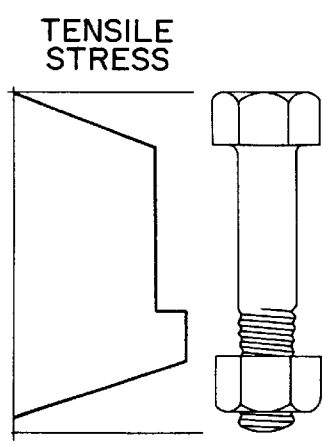
FIG. 6 shows the magnitude of tensile strength in a bolt, adopting the simplistic view often assumed in bolt calculations.
Figure 7:
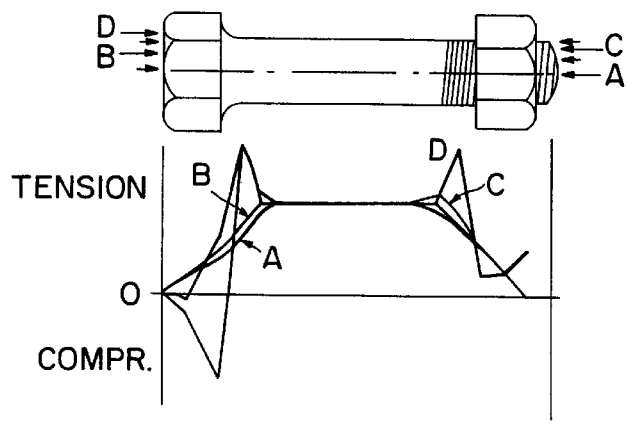
FIG. 7 is a view of the tensile stress along four lines parallel to the axis of the bolt.
Figure 5:
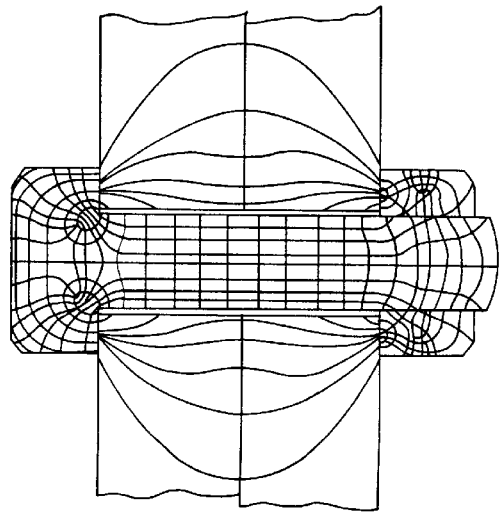
FIG. 5 shows the lines of tension and compression stress in a bolt loaded in pure tension (and the lines of principal compression stress in the joint)

Because the part of the ultrasonic wave 16 which is received by transducer 18 travels primarily down the central region of fastener 10, local stress concentrations near the surface under head 12 or in threads 15 have little effect in the received acoustic wave. Typical bolt stress distributions are illustrated in FIGS. 5, 6, and 7, which are copied from J. Bickford, "An introduction to the design and behavior of bolted joints," pages 15, 16, and 17, respectively (Marcel Dekker, Inc., New York, 1990).

Figure 8:
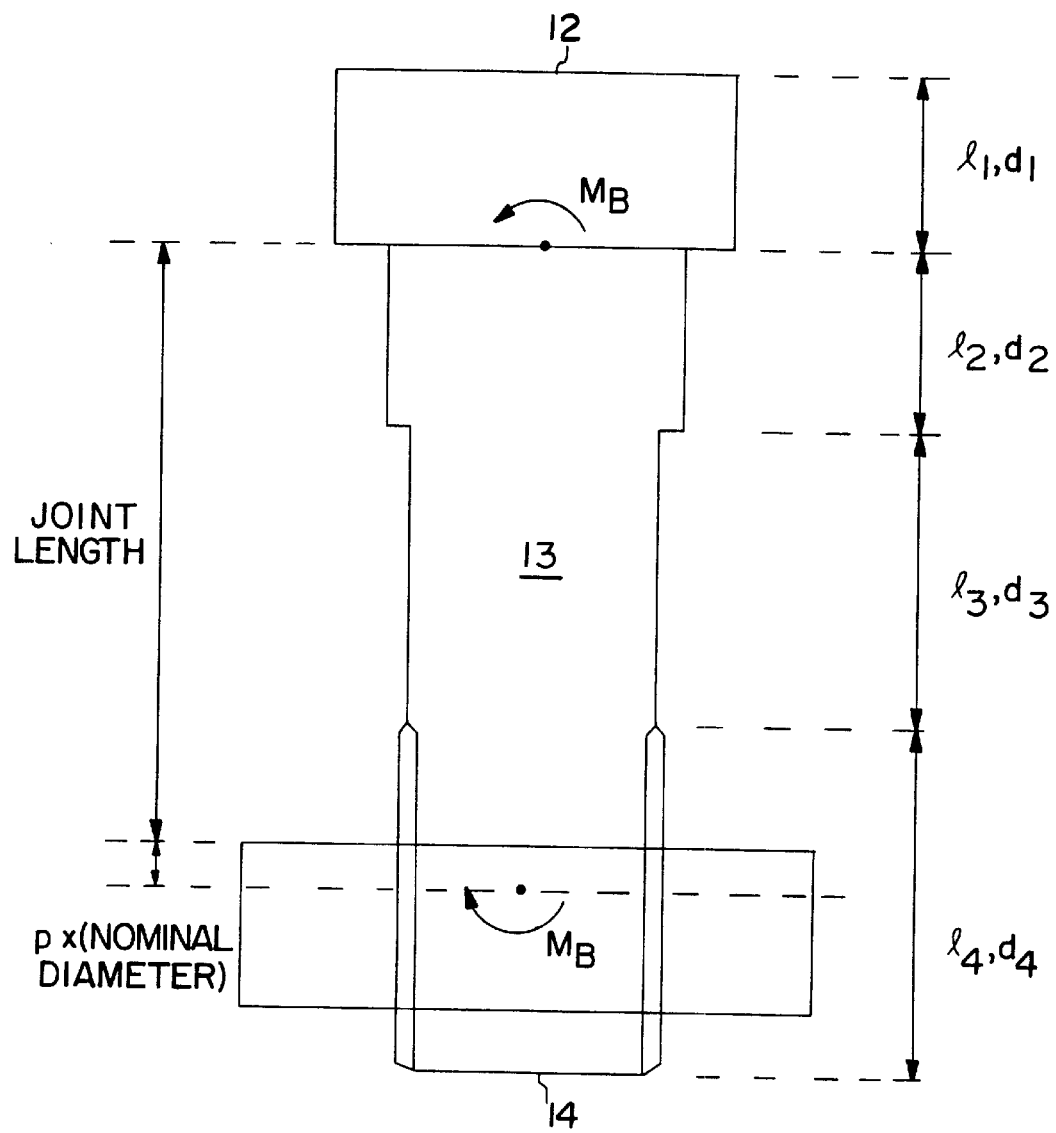
FIG. 8 illustrates a model of a fastener using cylindrical elements to represent each of the principal regions of the fastener.

The critical parameters affecting the behavior of fastener 10 under bending (i.e., the stresses and deflections) are the diameters (d) and lengths (l) of the various sections of the bolt shank. Therefore a simple model of a fastener 10 comprising cylindrical elements (see FIG. 8), which lends itself to both analytical and finite element stress analysis, was used for purposes of analysis. The major limitation of this model is that it is unable to handle the reduction in stress in shank 13 through the nut and head sections. In order to compensate for this effect, the effective length of the bolt under stress was increased to be the joint length plus a fraction "p" (typically 0.3 to 0.6) of the bolt diameter. This approach is often used in estimating the bolt effective stress length with ultrasonic bolt extensometers.

Effect on Ultrasonic Wave Measurements

Bending affects ultrasonic pulse-echo time-of-flight measurements in five ways:
  (i) The physical path length changes due to bolt deformation;
  (ii) The acoustic wave is redirected due to the angular deflection of the reflective surface at the end of the bolt;
  (iii) The acoustic wave is refracted due to stress gradients;
  (iv) The speed of sound changes as the wave travels through regions with additional stresses due to bending; and
  (v) Phase effects result from the oblique incidence of the wavefront received by the transducer.

Bolt Deformation

Figure 9:
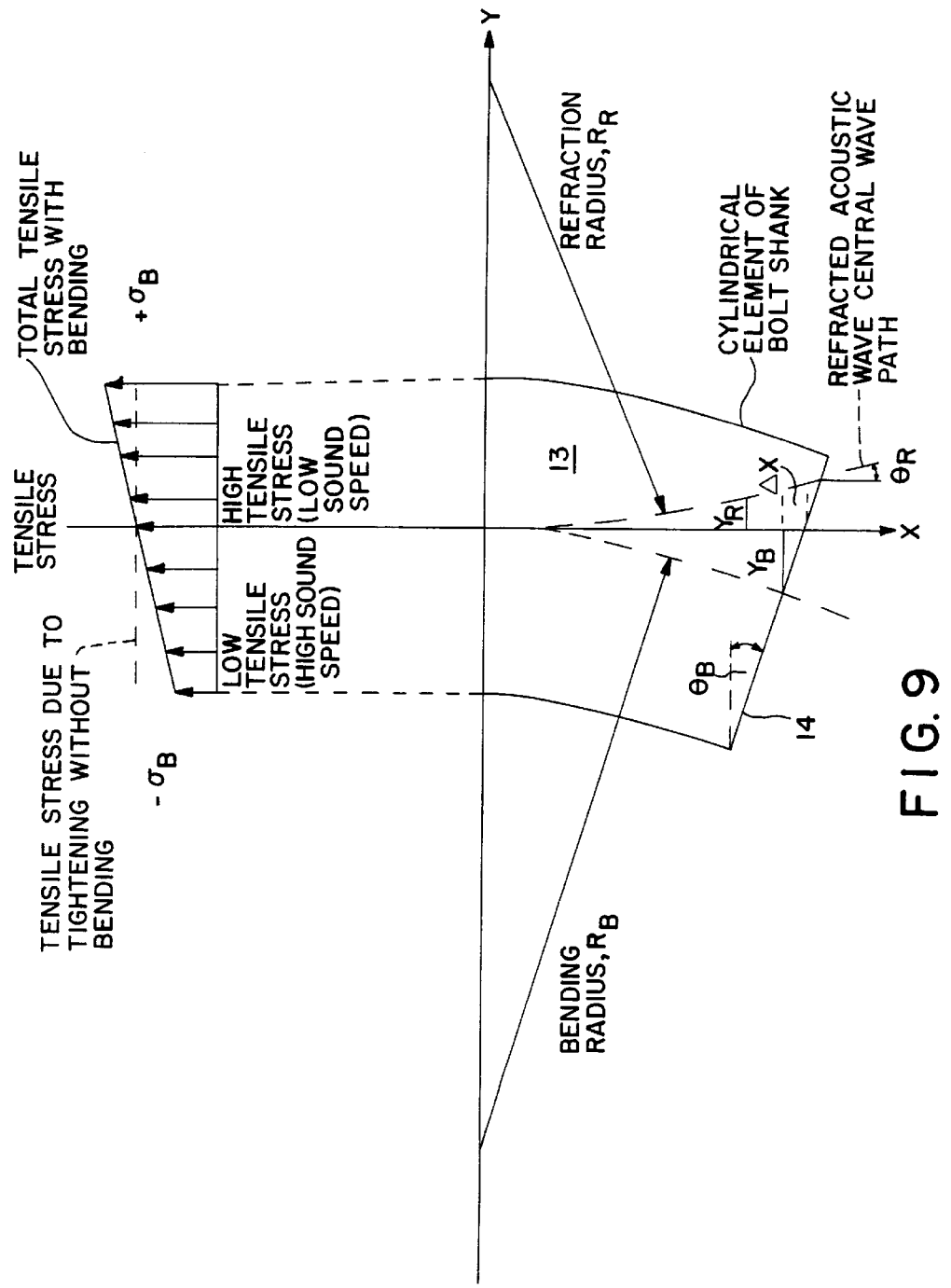
FIG. 9 shows the effect of bending on a cylindrical element such as that used to model the shank of a fastener.

When fastener 10 is subjected to a bending moment, M$_B$, axial stresses, linearly varying from compressive stress at one side of shank 13 to tensile stress at the opposite side, add to the tensile stresses resulting from tightening (see FIG. 9). Each cylindrical section of fastener 10 bends in an arc, of radius R$_B$, where:

$$R_B = \frac{EI}{M_B}$$

where E is the Modulus of Elasticity and I is the Moment of Inertia, which for a cylinder is:

$$I = \frac{\pi D^4}{64}$$

where D is the diameter of the cylindrical section.

The maximum additional fiber stress due to bending, σ$_B$, is:

$$\sigma_B = \frac{MD}{2I} = \frac{ED}{2R_B}$$

Because the change in stress across the bolt, Δσ, is 2σ$_B$, $$\Delta\sigma = \frac{ED}{R_B}$$

or $$R_B = \frac{ED}{\Delta\sigma}.$$

The end surface of this cylindrical element has linear deflection, y$_B$, where:

$$y_B = \frac{M_B l^2}{2EI}$$

where l is the length of the cylindrical section.

Without taking into account any effects of stress on the acoustic wave propagation, this results in an increase in the physical path length, Δx, of:

Δx=y$_B$ tan θ$_B$ where θ$_B$ is the angular deflection at the end of the section.

Acoustic Wave Redirection

The angular deflection, θ$_B$, at the end of the cylindrical section is given by:

$$\theta_B = \frac{M_B l}{EI}.$$

This angular deflection contributes to the total deflection angle of the reflective surface at end 14 of fastener 10 which, with a flat end surface, tends to redirect ultrasonic wave 16 away from transducer 18.

Refraction of the Acoustic Wave

No prior analysis of the effect of stress gradients on the propagation of acoustic waves in solids has been identified. The effect on the propagation of sound waves in atmospheric pressure gradients and water pressure gradients has been analyzed, however, using ray acoustics. See, e.g., A. Pierce, "Acoustics, an introduction to its physical principles and applications," pages 371–88 (McGraw-Hill, Inc., Woodbury, N.Y., 1989 Edition). Because the speed of sound in fastener materials varies linearly with stress, both these situations are analogous to the linear stress gradients in bolts subjected to bending.

When an ultrasonic wave is incident upon a region containing a stress gradient, the wave will be refracted toward the lower-sound-speed side (higher-tensile-stress-side) with an acoustic ray path radius of curvature $R_R$ (FIG. 9) given by:

$$R_R = \frac{v}{|\nabla_\perp v|}$$

where v is the speed of sound
or $$R_R = \frac{v}{(\Delta v / D)} = \frac{vD}{\Delta v}$$

where $\Delta v$ is the change in speed of sound across the bolt diameter, D. The ratio $$\frac{R_B}{R_R} = \frac{\Delta v}{vD} \cdot \frac{ED}{\Delta \sigma} = \frac{E}{v} \cdot \frac{\Delta v}{\Delta \sigma}$$

Because stress=E×strain, the change in stress across the bolt diameter is E times the change in strain across the bolt diameter, or $$\Delta \sigma = E \cdot \frac{\Delta l}{l},$$

so that $$\frac{R_B}{R_R} = \frac{\Delta v}{v} \cdot \frac{l}{\Delta l}.$$

Figure 9A:
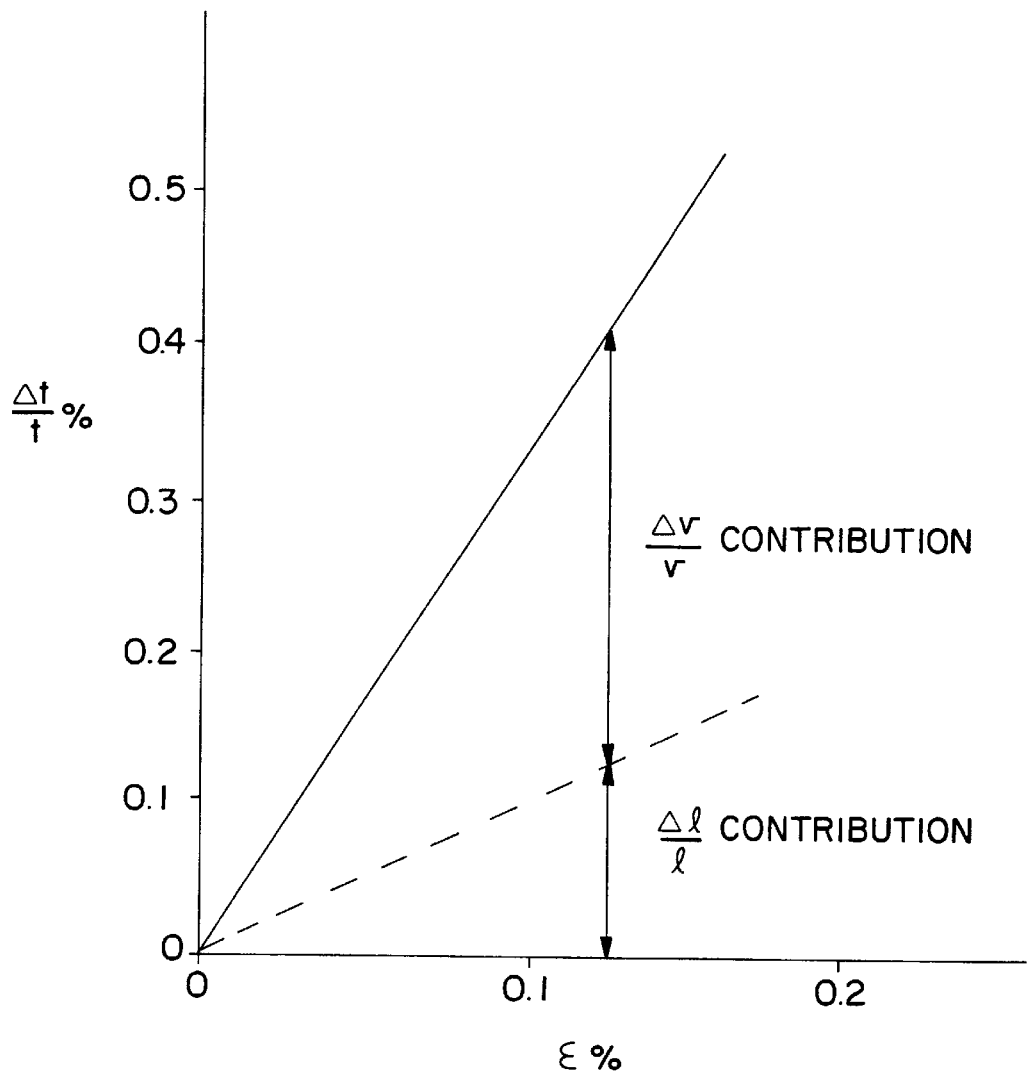
FIG. 9A is a graph of the percent change in time-of-flight ($\Delta t/t$) of an acoustic wave in steel versus percent strain E ($\Delta l/l$) showing the contributions of change in speed of sound ($\Delta v/v$) and strain ($\Delta l/l$).

Because $$\frac{\Delta t}{t} \approx \frac{\Delta v}{v} + \frac{\Delta l}{l},$$

where t is the time-of-flight and $\Delta t$ is the change in time-of-flight of the acoustic wave (as shown in FIG. 9A), the ratio $R_B/R_R$ is equal to the percentage change in the time-of-flight of the acoustic wave, due to the change in speed of sound, divided by the percentage change in the time-of-flight due to the elongation or strain. The ratio $R_B/R_R$ for longitudinal ultrasonic waves is approximately 2.2 for M 16×150, Grade 8.8, steel bolts.

In summary, when a bolt is subjected to a bending moment, the acoustic wave is refracted in the opposite direction to that of the bending of the bolt. The bending of the acoustic wave ray path is more severe than the bending of the bolt by a factor of about 2.2. Because the angles and deflections are small, the angles and deflections of the acoustic wave ray path can be assumed to be approximately −2.2 times those resulting from the bending of the bolt (i.e., 2.2 times, in the opposite direction).

Changes in the Speed of Sound

At the neutral axis of the bolt, there is no additional stress due to the bending moment on the bolt. The further from the neutral axis, the greater the positive or negative stress from bending—as illustrated in FIG. 9. Under bending, the central acoustic wave ray path deviates from the neutral axis towards the region of higher stress and, therefore, the region of lower speed of sound. Consequently, bending has the effect of increasing the time-of-flight by reducing the average speed of sound.

Phase Effects

Acoustic wave refraction and re-direction under bending causes the angle of incidence of the wavefront received by transducer 18 to be an oblique angle rather than 90°. The consequence of this is a phase difference across transducer 18 with an associated reduction in echo amplitude which can prevent reliable time-of-flight measurements. Furthermore, in more extreme cases, the amplitude can go through a null which can cause the pulse-echo instrumentation to "jump cycle" (i.e., start measuring to a different cycle of the received echo waveform). By "going through a null" is meant that the amplitude of the ultrasonic wave is reduced to zero due to acoustic waveform phase cancellation effects.

Model and Predictions

Ideally, a model should identify the surface contours of the ends of a fastener which, when the fastener is subject to bending, would (1) reflect the acoustic wave back to the transducer without any phase errors or any echo amplitude reduction, and (2) introduce no errors in the load calculated from the pulse-echo time-of-flight measurements. Unfortunately, this ideal is not possible because the contour that would best direct the acoustic wave back to the transducer under bending may not be the same as the contour which would result in no change in the time-of-flight under bending. The contours are similar, however, and the objective of the model is to predict both contours and to arrive at an optimum compromise solution.

Figure 10:
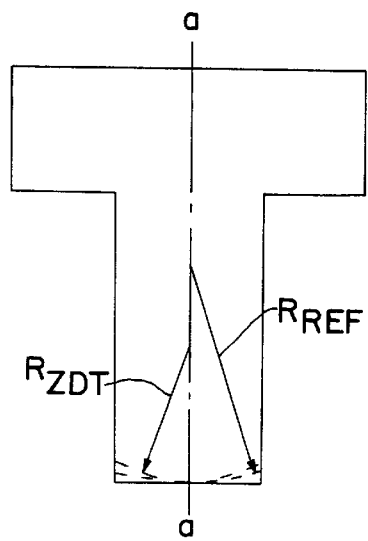
FIG. 10 shows the end surface contours of a fastener defined by the reflection radius, $R_{REF}$, and the zero change in time-of-flight radius, $R_{ZDT}$ ("zero delta T")

Both contours can be approximated as spherical surfaces. Because of inherent linearities (stress/strain, bending moment/deflections, stress/speed-of-sound), these surfaces are essentially independent of the amount of bending. Consequently, for a particular bolt and joint, the model identifies the radii of two spherical end surface contours: (1) $R_{REF}$, the radius of the surface contour that should direct the acoustic wave directly back to the transducer along the same path, and (2) $R_{ZDT}$, the radius of the surface contour that should result in zero change in the time-of-flight and, therefore, no error in ultrasonic load measurement (FIG. 10).

In one embodiment according to the present invention, a method of identifying a surface contour of a load bearing member includes first calculating the deflection of the second end relative to said first end of the load bearing member when said load-bearing member is subjected to asymmetric stress. Then, determining an incident ray path of said acoustic wave propagating from the first end to the second end when the load-bearing member is subjected to asymmetric stress. Next, defining the surface contour as a surface which reflects the acoustic wave back to the ultrasonic echo receiving means when the load-bearing member is subjected to asymmetric stress.

In another embodiment according to the present invention, a method of identifying a surface contour of a load bearing member includes first calculating the deflection of the second end relative to said first end of the load bearing member when said load-bearing member is subjected to asymmetric stress. Then, determining an incident ray path of said acoustic wave propagating from the first end to the second end when the load-bearing member is subjected to asymmetric stress. Next, the change in time-of-flight of the deflected acoustic wave is calculated. Finally, a surface contour is defined, where the surface contour minimizes the change in time-of-flight of the acoustic wave. The above steps occur while the load bearing member is subjected to asymmetric stress.

It is understood that while the contour may approximate an a spherical contour, the contour may take other forms. For example, the contour may approximate a parabola, an ellipse, or any other shape that will reflect an ultrasonic echo back to the transducer and result in minimal or no error in ultrasonic load measurement.

The model according to the present invention only takes into account the effect of bending on the central ray path of the acoustic wave. There will be some errors, of course, from variations across the wavefront due to the effect of distance from the neutral axis. The effects of these errors on the time-of-flight are expected to cancel to some extent; the major discrepancy between the model and reality caused by these variations will be the degree of amplitude reduction resulting from phase effects. Also, because only the central ray path is used for analysis, no assumptions are made in this model about the surface contour at the head of the bolt. The ray path analysis, upon which the model of the present invention is based, takes no account of diffraction of the acoustic wave.

The model was initially implemented using a computer spreadsheet. The following is a summary of the calculations. For each successive cylindrical section (n):

1. Cross-sectional area ($A_n$);
2. Moment of Inertia ($I_n$);
3. Angular deflection contribution of section n ($\theta_{Bn}$) resulting from bending moment M;
4. Linear deflection contribution of section n ($y_{Bn}$) resulting from bending moment M;
5. Average deflection of the neutral axis in section n (Average $y_B$) taking account of the deflections from previous sections;
6. Maximum stress in section n ($\tau_{Bn}$) resulting from bending moment M; and
7. Average speed of sound along the refracted acoustic wave central ray path in section n calculated from the stress gradient, the zero-stress speed of sound, and the change in speed of sound with stress.

For the entire fastener:

1. Total angular deflection of the end reflective surface ($\theta_B$) resulting from bending moment M (M is adjusted to give a total angular deflection of 1.0°);
2. Total linear deflection ($y_B$);
3. Acoustic wave central ray path length (P) taking into account the radii of curvature and the deflection of the end surface;
4. Average speed of sound of the acoustic wave central ray over the path length (Average v);
5. Error in the time-of-flight that would result with a flat end surface ($\Delta TOF$);
6. Reduction in geometric path length that would be required to reduce the error in the time-of-flight to zero ($\Delta x$);
7. Reflection radius ($R_{REF}$), the radius of the surface contour that is perpendicular to the incident acoustic wave ray path, which is defined by the linear deflection and angular deflection of the acoustic wave relative to the neutral axis, and is approximately equal to $y_B/\tan(\theta_B)$, where $y_B$ and $\theta_B$ are defined as above; and
8. Zero change in time-of-flight radius ($R_{ZDT}$), the radius of the surface contour that should result in zero change in the time-of-flight and, therefore, no error in ultrasonic load measurement during bending, is defined by the fastener length for zero change in time-of-flight and the linear deflection of the acoustic wave from the neutral axis, and is approximately equal to $((R_B/R_R+1)^2 Y_B^2 - \Delta X^2)/2\Delta X$, where $R_B$, $R_R$, and $\Delta X$ are defined as above.

Then, after $R_{REF}$ and $R_{ZDT}$ are calculated, at least a portion of one or both ends of a fastener are contoured. The contours have a radius of curvature equal to $R_{REF}$ or $R_{ZDT}$ depending on the particular attributes of the bolt and ultrasonic signal. A contour having a radius of curvature equal to $R_{REF}$ may show some error in time-of-flight measurements. Such a contour generally does not reduce ultrasonic wave amplitude, however, and reflects the signal directly back to the transducer. In contrast, a contour having a radius of curvature equal to $R_{ZDT}$ generally has zero error in time-of-flight measurements, but may reduce ultrasonic signal amplitude.

Consequently, for fasteners through which ultrasonic waves are expected to travel with little reduction in signal amplitude or when zero error in time-of-flight measurements is required, typically a contour having a radius of curvature equal to $R_{ZDT}$ would be applied to one or both ends of the fastener. In this way, time-of-flight measurements having zero error may be obtained. For fasteners through which ultrasonic waves are expected to travel with significant reduction in signal amplitude, however, typically a contour having a radius of curvature equal to $R_{REF}$ would be applied to one or both ends of the fastener. In this way, an ultrasonic signal is assured of being reflected back to the transducer, although some small error in ultrasonic load measurement may be present.

In any event, applying a contour having a radius of curvature equal to $R_{ZDT}$ or $R_{REF}$ to at least a portion of at least one end of a fastener helps to facilitate accurate and reliable ultrasonic load measurement.

In certain instances it may be advantageous to apply a radius of curvature approximately equal to a value somewhere between $R_{REF}$ and $R_{ZDT}$ as a compromise solution. Radii in this range would be used to simultaneously provide improved robustness in both amplitude and TOF measurement accuracy when compared with the nominally flat case. Table 1 lists $R_{REF}$ and $R_{ZDT}$ in both millimeters and as a percentage of total length for the fasteners under test. Typically, $R_{REF}$ is 50% ±10% of the length of the fastener and $R_{ZDT}$ is 40% ±10% of the length of the fastener. The total length of a fastener is equal to the fastener shank length plus the fastener head length. In Table 1, for example, Part No. 1026 (M8×1.25×50 Gd 10.9) is a metric bolt (M) having a shank diameter of 8 mm, a thread pitch of 1.25 mm, a shank length of 50 mm, and a steel grade quality of 10.9. That particular bolt has a head length of 5 mm, and a total length of 55 mm (50 mm +5 mm). The Reflection Radius percent (%) and Zero Change in Time-of-Flight Radius percent (%) are calculated as a percent (%) of the total length of the bolt, that is head length plus shank length.

TABLE 1

| PART NO. | BOLT | HEAD LENGTH | BOLT LENGTH | REF. RADIUS (mm) | REF. RADIUS % | ZDT RADIUS (mm) | ZDT RADIUS % |
|---|---|---|---|---|---|---|---|
| 1026 | M8 × 1.25 × 50 Gd. 10.9 | 5 | 55 | 28 | 51% | 22 | 40% |
| 1028 | M10 × 1.5 × 85 Gd. 10.9 | 6 | 91 | 46 | 50% | 37 | 40% |
| 5001 | M12 × 1.5 × 55 Gd. 10.9 | 9 | 64 | 32 | 50% | 25 | 39% |
| 5002 | M10 × 1.5 × 100 Gd. 12.9 | 7 | 107 | 56 | 53% | 44 | 41% |
| 5003 | M10 × 1.5 × 110 Gd. 12.9 | 11 | 121 | 68 | 56% | 55 | 45% |
| 5004 | M10 × 1.0 × 31 Gd. 10.9 | 11 | 42 | 19 | 46% | 15 | 36% |
| 5005 | M12 × 1.5 × 95 Gd. 8.8 | 10 | 105 | 53 | 51% | 42 | 40% |
| 5006 | M12 × 1.5 × 44 Gd. 10.9 | 6 | 50 | 30 | 60% | 26 | 52% |
| 5007 | M10 × 1.5 × 40 Gd. 10.9 | 8 | 48 | 23 | 49% | 20 | 41% |
| 5008 | M12 × 1.5 × 90 Gd. 10.9 | 4 | 94 | 49 | 52% | 39 | 41% |
| 5009 | M10 × 1.5 × 20 Gd. 10.9 | 9 | 29 | 11 | 40% | 9 | 30% |
| 5012 | M10 × 1.5 × 90 Gd. 10.9 | 3 | 93 | 46 | 50% | 35 | 38% |
| 5013 | M12 × 1.5 × 90 Gd. 10.9 | 7 | 97 | 49 | 51% | 38 | 39% |
| 5014 | M14 × 1.5 × 120 Gd. 10.9 | 7 | 127 | 61 | 48% | 46 | 36% |
| 5015 | M12 × 1.75 × 55 Gd. 8.8 | 9 | 64 | 31 | 49% | 26 | 40% |
| 5016 | M12 × 1.5 × 40 Gd. 10.9 | 8 | 48 | 24 | 50% | 21 | 43% |
| 50552 | M12 × 1.75 × 55 Gd. 10.9 | 6 | 61 | 32 | 52% | 27 | 44% |
| 50560 | M10 × 1.5 × 25 Gd. 10.9 | 8 | 33 | 17 | 53% | 16 | 47% |
| 50561 | M12 × 1.5 × 105 Gd. 10.9 | 2 | 107 | 54 | 50% | 41 | 38% |
| 50562 | M10 × 1.5 × 20 Gd. 10.9 | 5 | 25 | 13 | 53% | 12 | 46% |
| 50576 | M12 × 1.75 × 100 Gd. 10.9 | 7 | 107 | 52 | 49% | 39 | 37% |
| 5428 | M10 × 1.5 × 35 Gd. 10.9 | 6 | 41 | 22 | 55% | 18 | 44% |
| 6108891300 | M10 × 1.5 × 70 Gd. 10.9 | 6 | 76 | 40 | 52% | 32 | 42% |
| 7666 | M8 × 1.25 × 25 Gd. 10.9 | 5 | 30 | 15 | 50% | 11 | 38% |
| 7667 | M14 × 2.0 × 55 Gd. 8.8 | 8 | 63 | 29 | 46% | 23 | 36% |
| 7671 | M18 × 1.5 × 205 Gd. 12.9 | 17 | 222 | 113 | 51% | 84 | 38% |
| 7672 | M22 × 1.5 × 85 Gd. 10.9 | 16 | 101 | 53 | 53% | 43 | 42% |
| 7673 | M12 × 1.5 × 105 Gd. 12.9 | 9 | 114 | 62 | 54% | 50 | 44% |
| 7674 | M10 × 1.25 × 75 Gd. 10.9 | 9 | 84 | 43 | 51% | 31 | 37% |
| 7675 | M24 × 2.0 × 240 Gd. 10.9 | 15 | 255 | 145 | 57% | 115 | 45% |
| 7676 | M10 × 1.5 × 90 Gd. 8.8 | 5 | 95 | 45 | 48% | 33 | 35% |
| 7677 | M10 × 1.5 × 100 Gd. 8.8 | 6 | 106 | 51 | 48% | 37 | 35% |
| 7678 | M10 × 1.5 × 110 Gd. 8.8 | 6 | 115 | 63 | 54% | 47 | 41% |
| 7882 | M12 × 1.75 × 135 Gd. 11.9 | 6 | 141 | 74 | 53% | 59 | 42% |
| | | | | Average | 51% | | 40% |

Experimental Verification of Model Predictions

Figure 11:
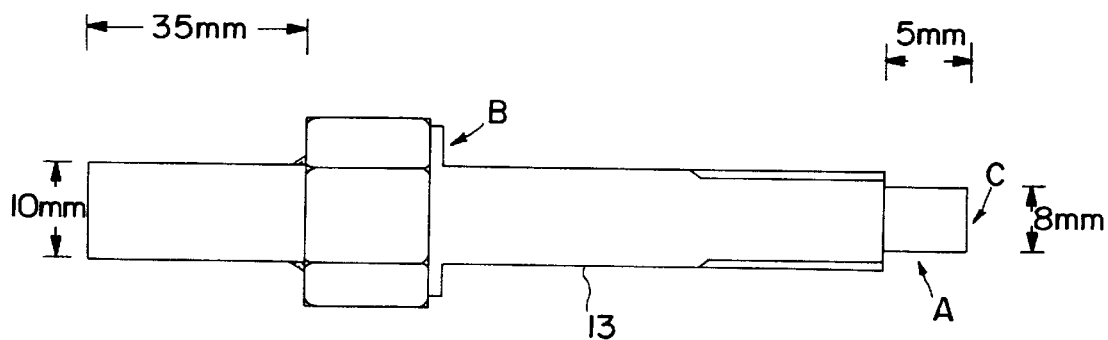
FIG. 11 is a modified bolt used to verify linear and angular deflection under bending.

In order to verify that the fasteners do, in fact, behave as predicted when tightened in a joint with non-parallel joint bearing surfaces, a number of bolts (Ultrafast bolt Part No. 6108891300; M 10×70×1.5) were modified to incorporate measurement reference surfaces (surfaces "A," "B," and "C" in FIG. 11) and tightened in joints with 1° and 2° angled washers. Linear and angular deflections were measured at the end of the bolt. The following was concluded from analysis of the results:

1. The measured deflections were almost identical to those predicted. The bending radii calculated from the deflection measurements varied between 38 mm and 45 mm. The model predicted 40 mm for this bolt and joint. This confirmed the assumption that the bolt moves freely in the radial direction during tightening with non-parallel joint bearing surfaces and gave an indication of the accuracy of the model.
2. With a conventional nut and hard joint, the bolt typically only experiences about 50 % of the angle introduced into the joint due to thread clearance and deformation.
3. Approximately 30% of the torque at yield was required to produce about 1° bending in the bolt. This also correlates with the model predictions for the bolt.

Fasteners identified by Ultrafast bolt Part No. 6108891300 (M10×1.5×70) were predicted by the model to have an $R_{REF}$ of 40 mm and an $R_{ZDT}$ of 32 mm. Bolts with a 76 mm head radius (100% of the bolt length) were machined to end radii of 30 mm, 34 mm, 38 mm, 42 mm, and 46 mm and bending accuracy tests were performed with both 1° and 2° angled washers. The analysis of the data from these tests is summarized in the graphs of FIGS. 12A–12F. All tests illustrated in FIGS. 12A–12F were performed on Ultrafast bolt Part No. 6108991300 (M10×1.5×70).

Figure 12A:
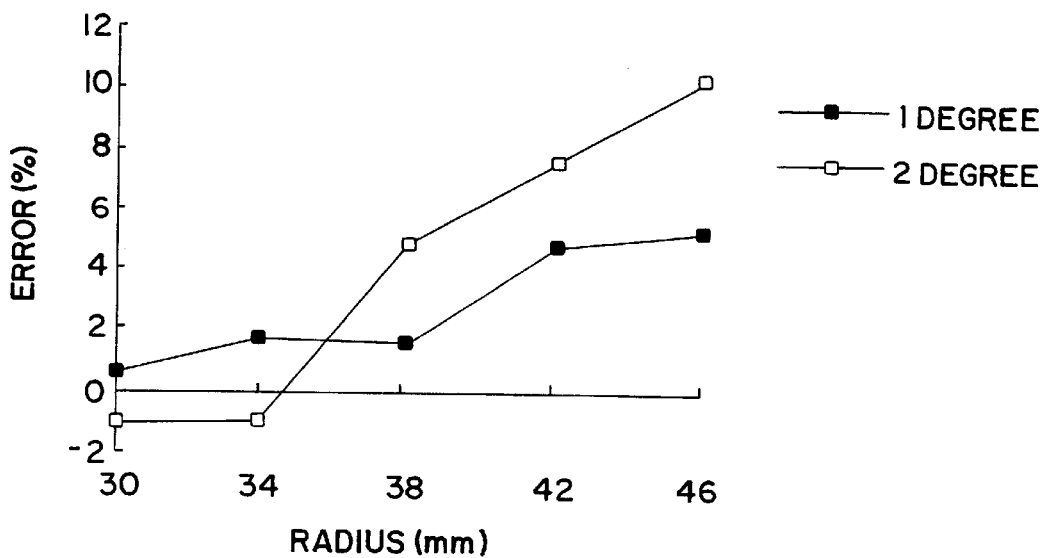
FIG. 12A is a graph of error (%) in ultrasonically determined load as a function of the radius (mm) of a spherical contour applied to the end of a bolt and illustrates data which resulted from bending accuracy tests done on Ultrafast bolt Part No. 6108891300 (M10×1.5×70) having a spherical contour on its head with a radius of 76 mm.

FIG. 12A is a graph showing the percent (%) error in ultrasonically determined load as a function of the radius (mm) of a spherically contoured end of a bolt. As shown, at 30 and 34 mm end radii there was less than 2% error in load measurement for bolts subjected to 1° and 2° bending. Thus, the accuracy was highest (less than 2% error) at 30 mm and 34 mm end radii as predicted by the model. This bolt is qualified at 1° and 2° bending with either of these designs. An error of approximately +5% occurred at 2° bending for a bolt having 38 mm end radii at the predicted $R_{REF}$. There may be less waveform distortion at this radius, however, which may make it easier to make reliable pulse-echo measurements with some bolts.

Figure 12B:
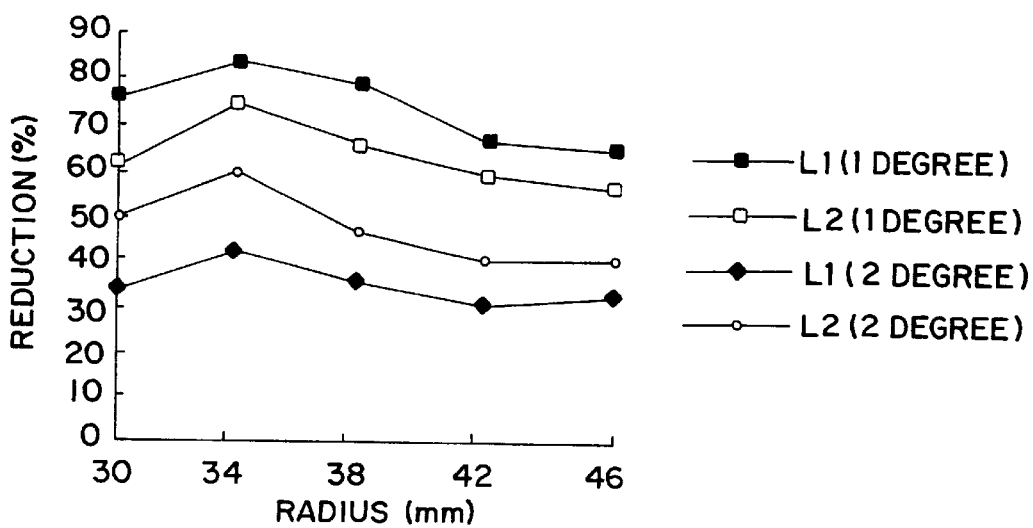
FIG. 12B is a graph of L1, the first longitudinal echo, and L2, the second longitudinal echo, amplitude reductions (%) as a function of the radius (mm) of a spherical contour applied to the end of a bolt and illustrates data which resulted from bending accuracy tests done on Ultrafast bolt Part No. 6108891300 (M10×1.5×70) having a spherical contour on its head with a radius of 76 mm.

FIG. 12B is a graph of the reduction in amplitude of L1, a longitudinal echo that travels up and down a fastener one time, and L2, a longitudinal echo that travels up and down a fastener two times, as a function of the radii (mm) of a spherically contoured bolt ends. At 1° bending, moderate percent (%) reduction in amplitude of L1 and L2 (from 100% at no bending to 85–65% for L1; and from 100% at no bending to 75–55% for L2) occurred for bolts having 30 mm, 34 mm, 38 mm, 42 mm, and 46 mm spherically contoured end radii. A slightly more significant percent (%) reduction in amplitude of L1 and L2 (from 100% at no bending to 45–35% for L1; and from 100% at no bending to 60–45% for L2) occurred a 2° bending for these bolts. Note that the percent (%) reduction in amplitude for L2 was less than the percent (%) reduction for L1 at 2° bending. Also, in each instance, the smallest percent (%) reduction occurred in bolts having 34 mm spherically contoured end radii. In any event, because none of these bolts received echoes having wave amplitudes near null, reliable and accurate load measurements can be made at 1° and 2° bending.

Figure 12C:
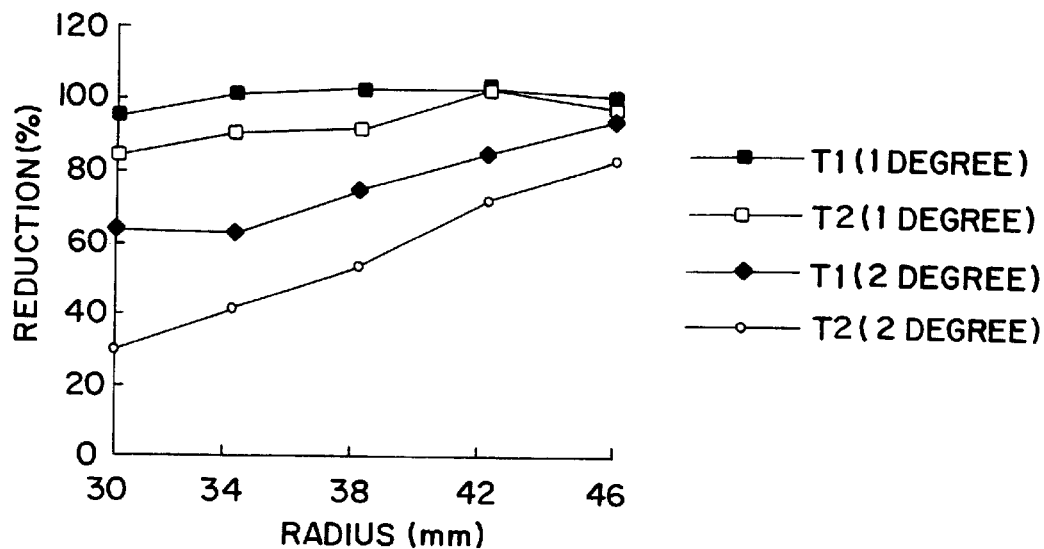
FIG. 12C is a graph of T1, the first transverse echo, and T2, the second transverse echo, amplitude reductions (%) as a function of the radius (mm) of a spherical contour applied to the end of a bolt and illustrates data which resulted from bending accuracy tests done on Ultrafast bolt Part No. 6108891300 (M10×1.5×70) having a spherical contour on its head with a radius of 76 mm.

FIG. 12C is a graph of the reduction in amplitude of T1, a transverse echo that travels up and down a fastener one time, and T2, a transverse echo that travels up and down a fastener two times, as a function of the radii (mm) of a spherically contoured end of a bolt. At 1° bending, T1 and T2 showed a small percent (%) reduction in amplitude (from 100% at no bending to approximately 99% for T1; and from 100% at no bending to 85% for T2) for bolts having 30 mm, 34 mm, 38 mm, 42 mm, and 46 mm spherically contoured end radii. Note that the percent (%) reduction in amplitude for T1 did not occur for bolts having 34 mm, 38 mm, and 42 mm spherically contoured end radii at 1° bending. Similarly, there was no percent (%) reduction in amplitude for T2 for bolts having a 42 mm end radius at 1° bending. Moderate percent (%) reduction in amplitude of T1 and T2 (from 100% at no bending to 95–60% for T1; and from 100% at no bending to 85–30% for T2) occurred a 2° bending for these bolts. At 2° bending, the percent (%) reduction in amplitude generally decreased with increasing bolt end radii of curvature. In any event, because none of these bolts showed echoes having amplitudes reduced to near null, reliable and accurate load measurements can be made at 1° and 2° bending. In addition, the percent (%) reduction in T1 and T2 was much less than the percent (%) reduction of L1 and L2 (shown in FIG. 12B) indicating that transverse waves are less affected by bending than longitudinal waves.

Figure 12D:
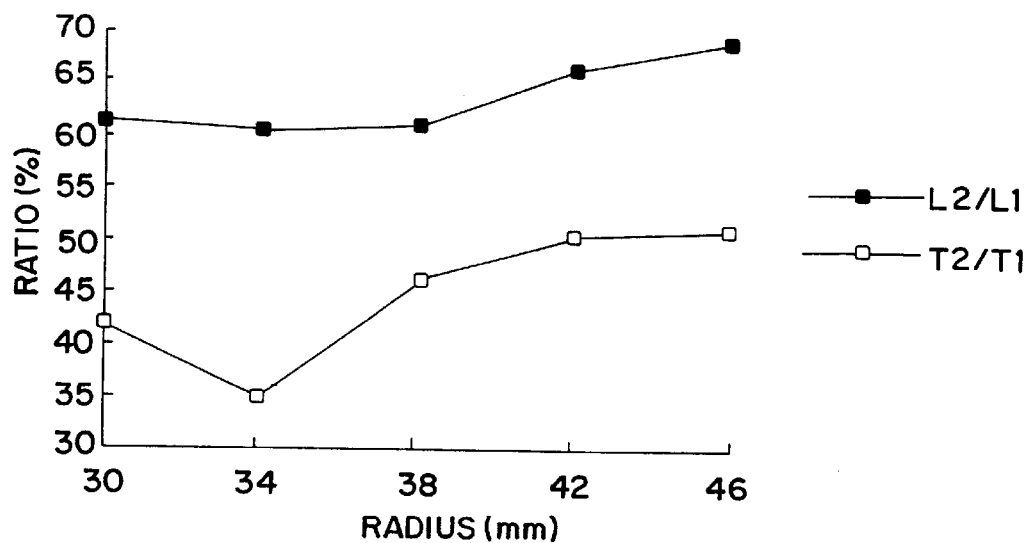
FIG. 12D is a graph of echo amplitude ratios L2/L1 and T2/T1 (%) as a function of the radius (mm) of a spherical contour applied to the end of a bolt and illustrates data which resulted from bending accuracy tests done on Ultrafast bolt Part No. 6108891300 (M10×1.5×70) having a spherical contour on its head with a radius of 76 mm.

FIG. 12D is a graph of echo amplitude percent (%) ratios L2/L1 and T2/T1 as a function of radius (mm) for spherically contoured ends of a bolt. An L2/L1 or T2/T1 near 1.0 would indicate little or no reduction in the amplitude of L2 or T2 echoes as compared to the amplitude of L1 and T1 echoes, whereas a 0.0 would indicate that L2 or T2 was reduced to null. As shown in FIG. 12D, the ratios of L2/L1 and T2/T1 ranged from 62–70% and 35–52%, respectively, for bolts having end radii of 30 mm, 34 mm, 38 mm, 42 mm, and 46 mm. This indicates that L2 and T2 echoes were not reduced to null.

Figure 12E:
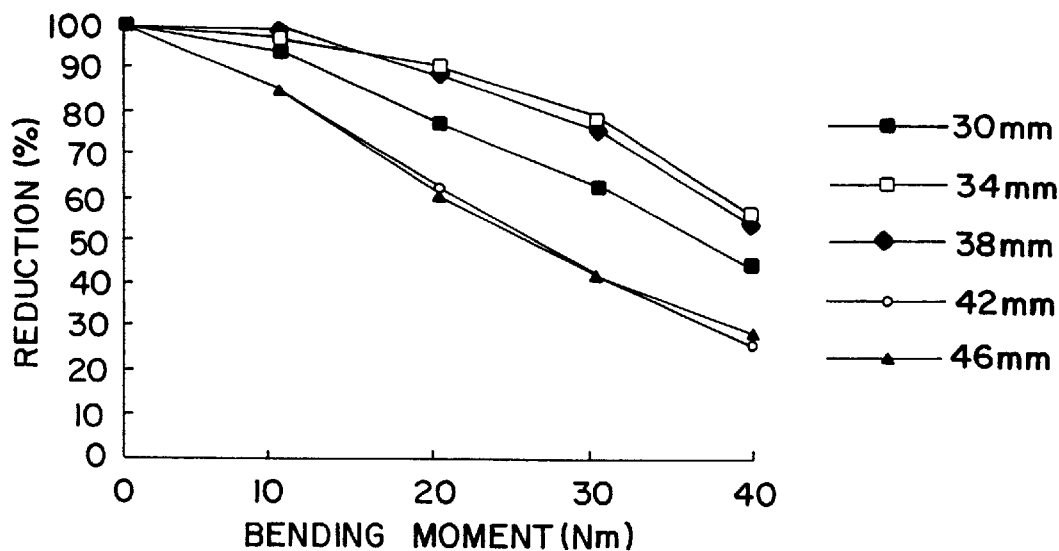
FIG. 12E is a graph of L1 echo amplitude reduction (%) as a function of the Bending Moment (Nm) applied to a bolt and illustrates data which resulted from bending accuracy tests done on Ultrafast bolt Part No. 6108891300 (M10× 1.5×70) having a spherical contour on its head with a radius of 76 mm.

FIG. 12E is a graph of L1 echo amplitude percent (%) reduction as a function of the Bending Moment (Nm) applied to a bolt and illustrates data which resulted from bending accuracy tests. As shown in FIG. 12E, L1 echo amplitude was reduced from 100% at zero bending moment to about 30–60% at 40 Nm bending moment for bolts having spherically contoured end radii of 30 mm, 34 mm, 38 mm, 42 mm, and 46 mm. This data indicates that L1 was not reduced to null and, therefore, accurate and reliable load measurements on a fastener can be obtained under bending.

Figure 12F:
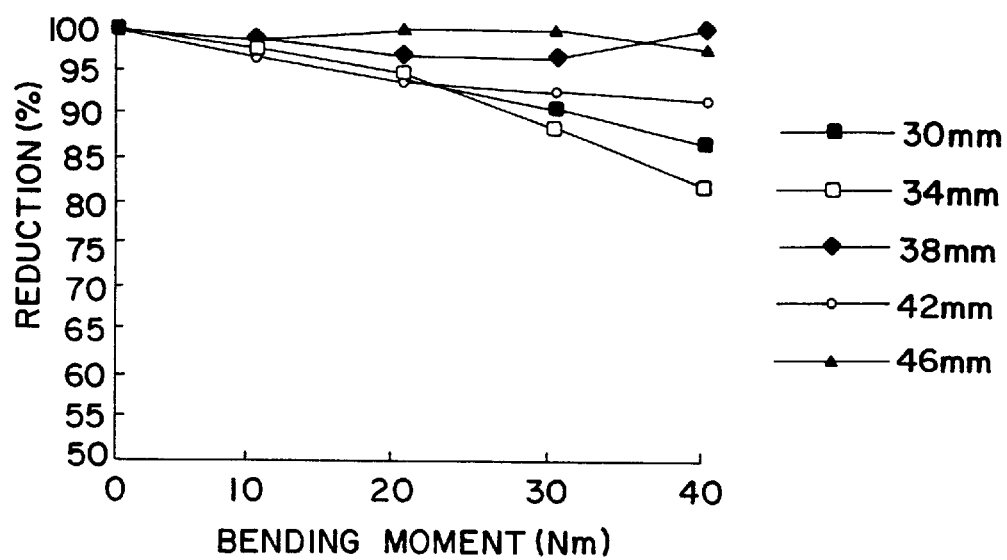
FIG. 12F is a graph of T1 echo amplitude reduction (%) as a function of the Bending Moment (Nm) applied to a bolt and illustrates data which resulted from bending accuracy tests done on Ultrafast bolt Part No. 6108891300 (M10× 1.5×70) having a spherical contour on its head with a radius of 76 mm.

FIG. 12F is a graph of T1 echo amplitude reduction (%) as a function of the Bending Moment (Nm) applied to a bolt and illustrates data which resulted from bending accuracy tests. As shown in FIG. 12F, T1 echo amplitude was reduced from 100% at zero bending moment to about 83–99% at 40 Nm bending moment for bolts having spherically contoured end radii of 30 mm, 34 mm, 38 mm, 42 mm, and 46 mm. Again, this data indicates that accurate and reliable load measurements on a fastener can be obtained under bending because none of the observed amplitudes was reduced to null. Also, as shown above, transverse signals appear to maintain their amplitude under bending better than longitudinal signals.

These test results indicate that the model of the present invention can be used to predict optimum fastener end surface geometries with good accuracy. This model only considers the acoustic wave central ray path and, therefore, its predictions do not take account of, nor are they affected by, head (or transducer) end surface geometry. All tests using the end radii predicted in this model have used head radii of 100% of the length of the bolt. Ignoring the effects of diffraction, this radius focuses the acoustic beam to the end surface.

End Surface Geometry

As discussed above, received echoes will reduce in amplitude as a fastener is bent until they reach a null point at some bending angle. In order to make accurate and reliable ultrasonic measurements, it is important not to operate in the region close to the null. The model of the present invention permits fastener designs that preserve the integrity of received echoes in the presence of bending. The model calculates the radius or other contour of the surfaces of at least one of head 12 and threaded end 14 of fastener 10. By placing a radius or other contour on these surfaces, the bending angle at which received echoes reach a null may be increased and the sensitivity of the echoes to bending stresses may be reduced.

The model includes, but is not limited to, designs in which a spherical contour with a radius of curvature equal to the length of fastener 10 is placed on end 14, head 12, or both head 12 and end 14 of fastener 10. The model was tested, as discussed above, on fasteners 10 having a spherical end 14 and a spherical head 12. A variety of other configurations may be suitable.

Figure 13A:
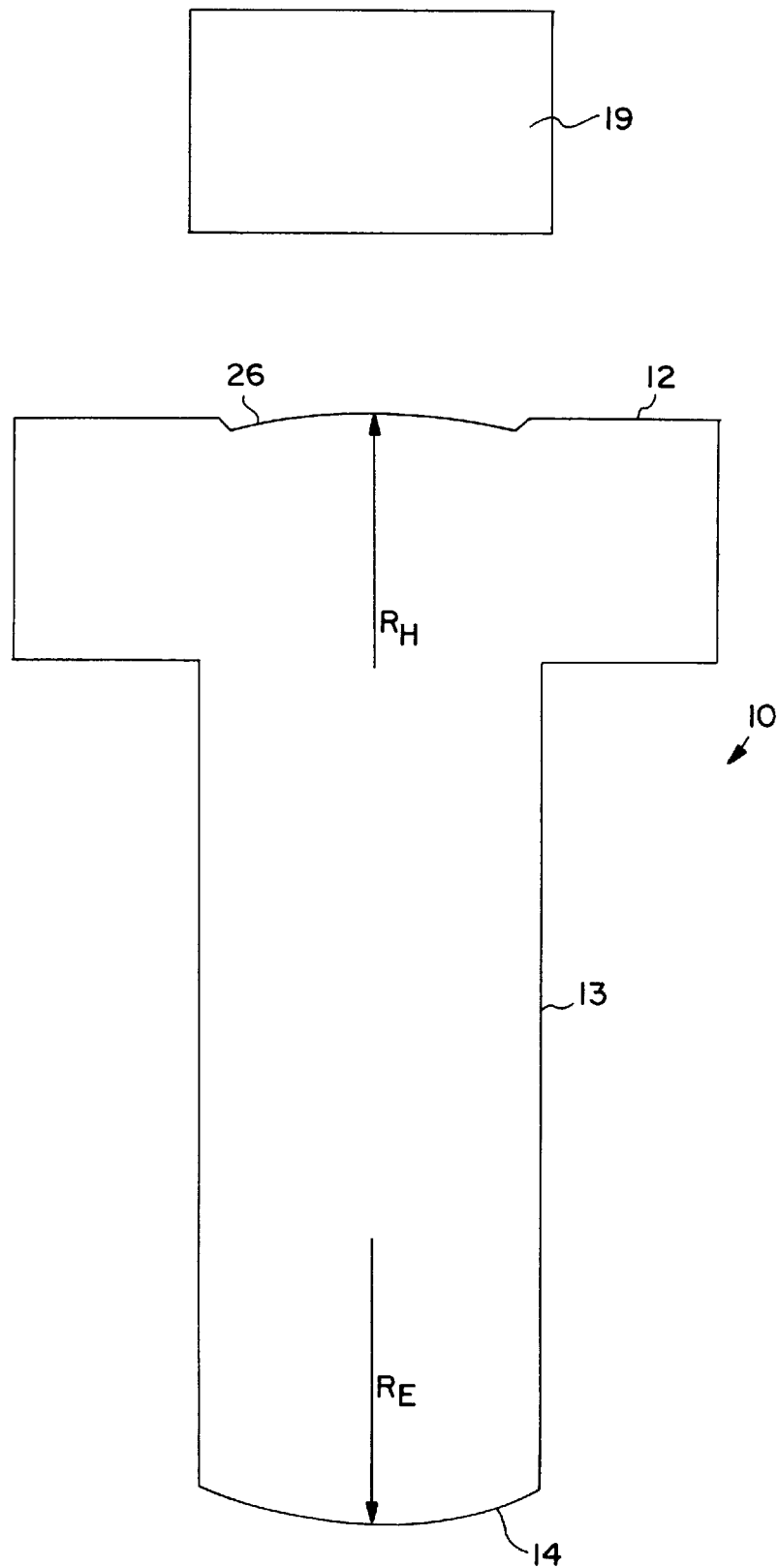
FIGS. 13A and 13B illustrate a preferred embodiment of the fastener design according to the present invention in which the sum of the spherical head radius (RH) and the spherical end radius (RE) of the fastener equals the length of the fastener, without a transducer (FIG. 13A) and with a transducer permanently affixed to the head of the fastener (FIG. 13B)
Figure 13B:
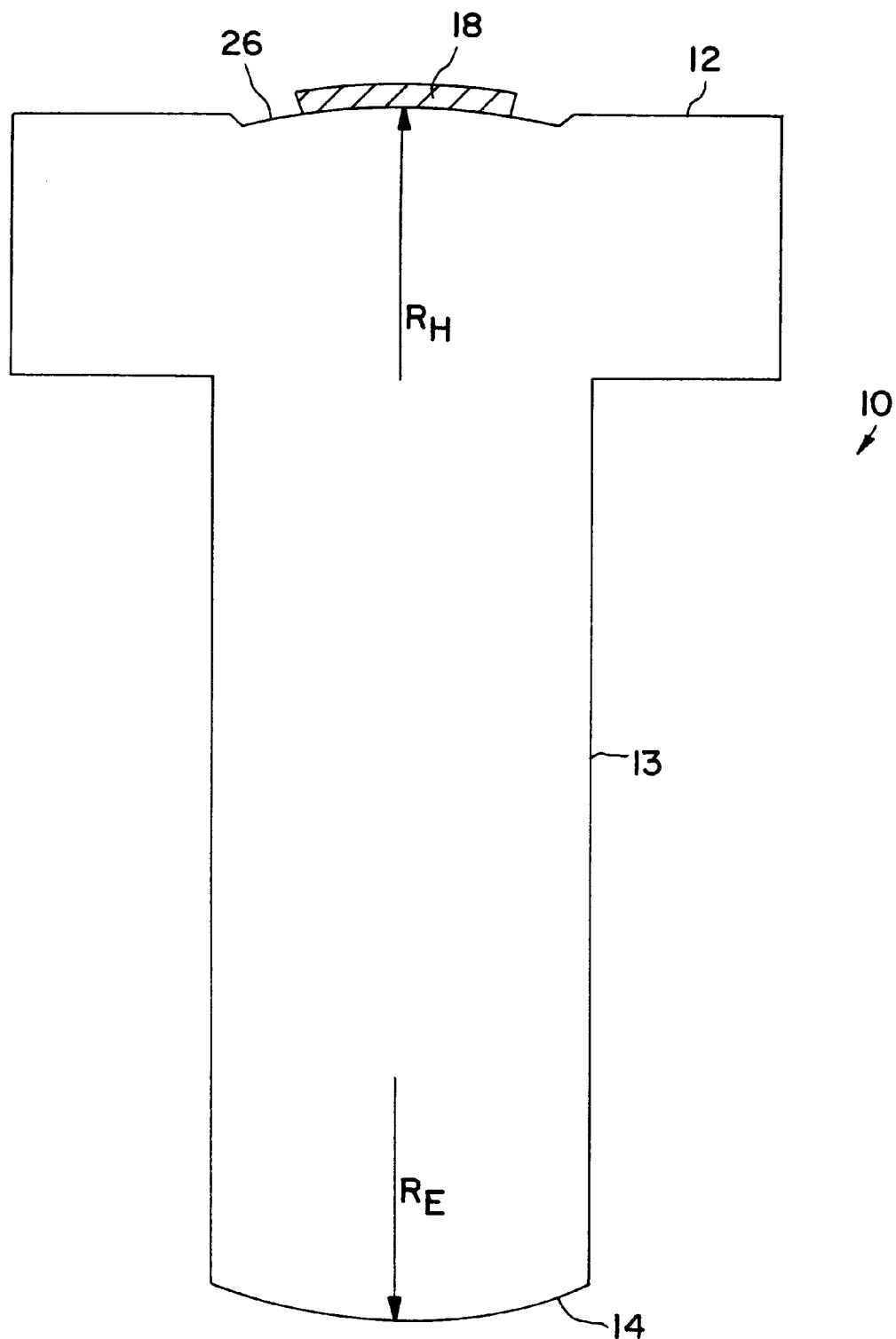

In the preferred embodiment of the fastener design according to the present invention, fastener 10 has a spherical surface 26 on head 12 of radius ($R_H$) equal to the length of fastener 10 minus the radius ($R_E$) of end 14. That is, the sum of the radius of curvature of spherical surface 26 and the radius of curvature of end radius 14 is equal to the length of fastener 10. Such a configuration is illustrated in FIGS. 13A and 13B. This may be an optimum configuration because it provides for constant geometric path length and, therefore, minimum echo amplitude reductions with multiple echoes of ultrasonic signals.

It is understood that the present invention may used with any device that will both transmit and receive ultrasonic signals through fastener 10. For example, ultrasonic signals may be transmitted and received with an electromagnetic transducer or a piezoelectric transducer 18 (see FIG. 13D) adjacent fastener 10. Ultrasonic transducer 18 is permanently affixed (as in FIG. 13B) to fastener 10. It is understood that ultrasonic signals may also be transmitted and received with a laser 19 (see FIG. 13A) adjacent fastener 10. Furthermore, bending performance with this design is unaffected by whether the ultrasonic wave transmitter and receiver is on head 12 or threaded end 14 of fastener 10. The remainder of the non-limiting embodiments describe the invention used with piezoelectric transducers 18 removably or permanently affixed to fastener 10, although it is understood that ultrasonic signals may be transmitted and received using other means of ultrasonic signal transmission and reception such as electromagnetic transducers or lasers.

The contoured surfaces 12 and 14 of fastener 10 provide two advantages: they focus ultrasonic wave 16 and, if the contours are appropriately selected, the end surfaces maximize the amount of signal returned to ultrasonic transducer 18 as shown in FIG. 13B. Otherwise, symmetrical bending stresses may preclude any signal from reaching ultrasonic transducer 18 and, even if a signal is obtained, bending may distort that signal. A tradeoff exists between determination of $R_{REF}$, the radius of curvature assuring that ultrasonic transducer 18 will receive some reflected signal, and $R_{ZDT}$, the radius of curvature assuring that the signal has minimal error. In some applications, the design might optimize $R_{REF}$ to assure that ultrasonic transducer 18 receives some reflected signal—even if that signal is not the most accurate. For the test results outlined above, $R_{REF}$ is typically about 50% of the length of the fastener and $R_{ZDT}$ is about 40% of the length of the fastener. These percentages will change, of course, depending upon the particular fastener. A suitable range of $R_{REF}$ and $R_{ZDT}$ for a number of different fasteners is approximately 25–70%, preferably approximately 30–60% of the length of the fastener.

Figure 13C:
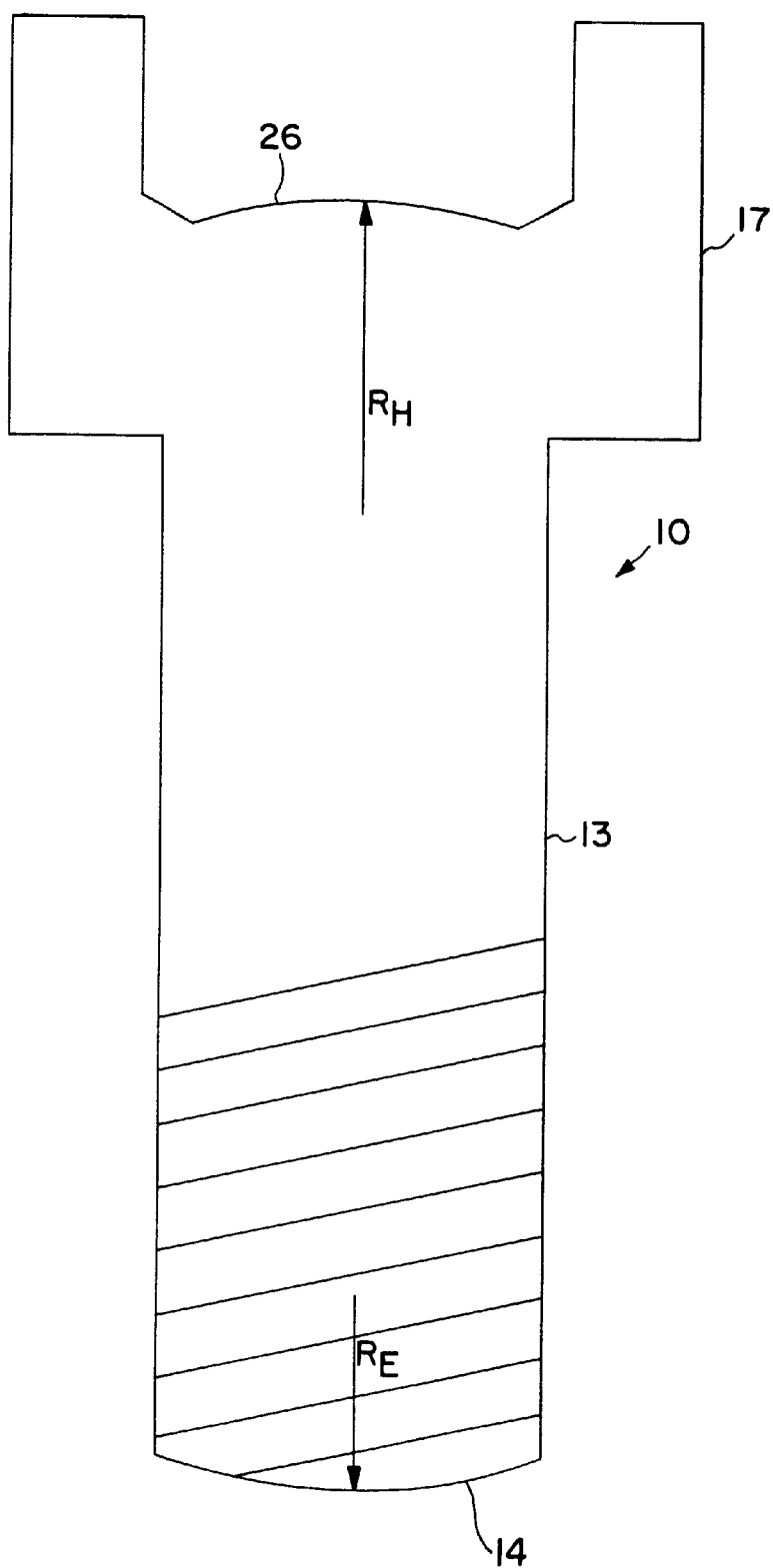
FIG. 13C illustrates another embodiment of the fastener design according to the present invention with a spherical head radius (RH) and a spherical end radius (RE), and an internal drive head.

In another embodiment, fastener 10 has an internal drive head or lightening hole recess 17 having a spherically contour 26 over a portion of the internal surface of recess 17, and a spherically contoured end surface 14. See FIG. 13C. Where the internal recess serves only to reduce the weight of fastener 10, recess 17 serves as a lightening hole.

Fastener 10 may have a contoured end 14 and a flat head 12. The flat head is easier to form in the manufacture of internal drive screws and may be desired in some applications.

Figure 13D:
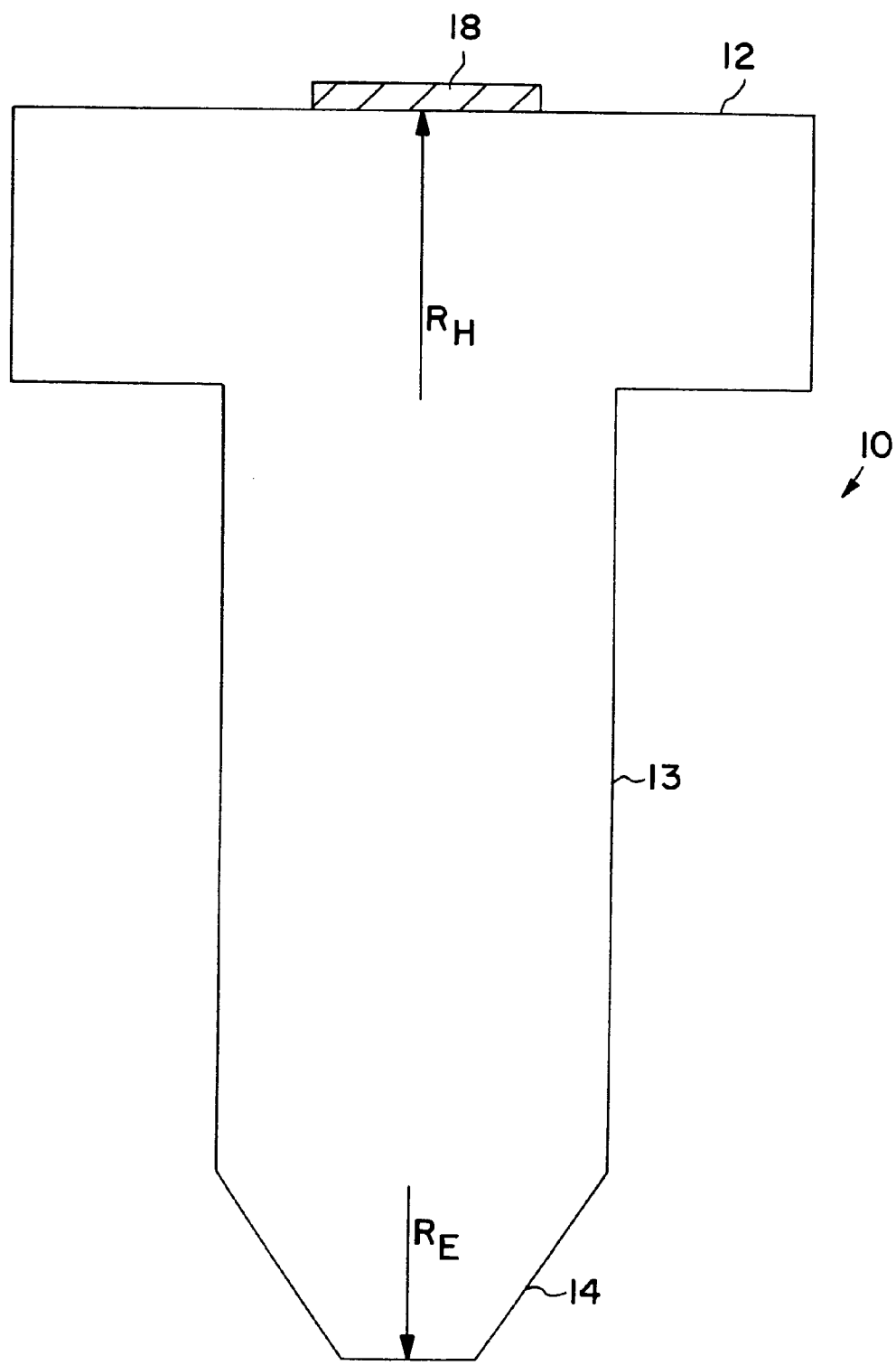
FIG. 13D illustrates an embodiment of the fastener design according to the present invention with a spherical end radius (RE) over a portion of the chamfered or pointed end of the fastener, and a flat head having a transducer removably or permanently affixed thereto.

For example, FIG. 13D shows another embodiment of fastener 10 according to the present invention. In this embodiment, fastener 10 has a spherical end radius ($R_E$) over a portion of the end of fastener 10, and a flat head having a transducer 18 removably or permanently affixed thereto. When transducer 18 is removably attached, it is preferred to use a flat head to engage the flat surface of the transducer. Alternatively, only a portion of the head (as shown in FIG. 13A) or end (as shown in FIG. 13D) of the fastener 10 may be contoured such as for use with chamfered, or pointed fasteners (as in FIG. 13D) as used in automated feeding equipment.

Figure 14:
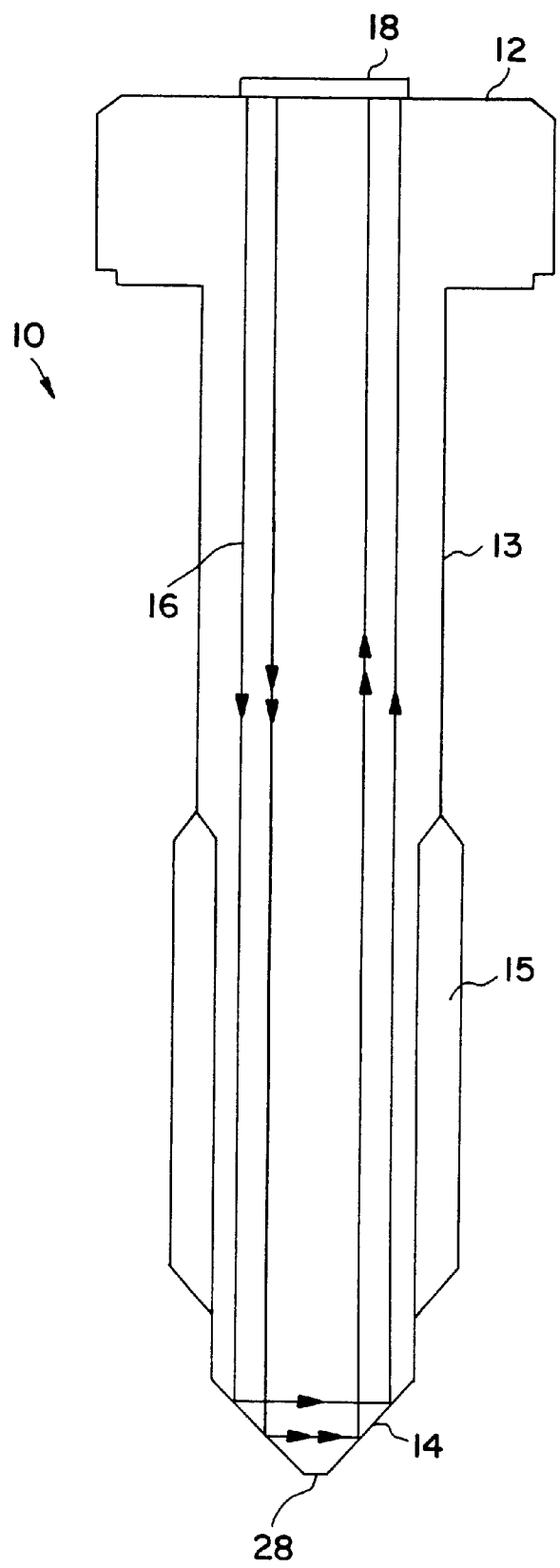
FIG. 14 shows, for a fastener not subject to bending, an alternative embodiment of the fastener design according to the present invention in which the fastener end has a 90 degree conical point.
Figure 16:
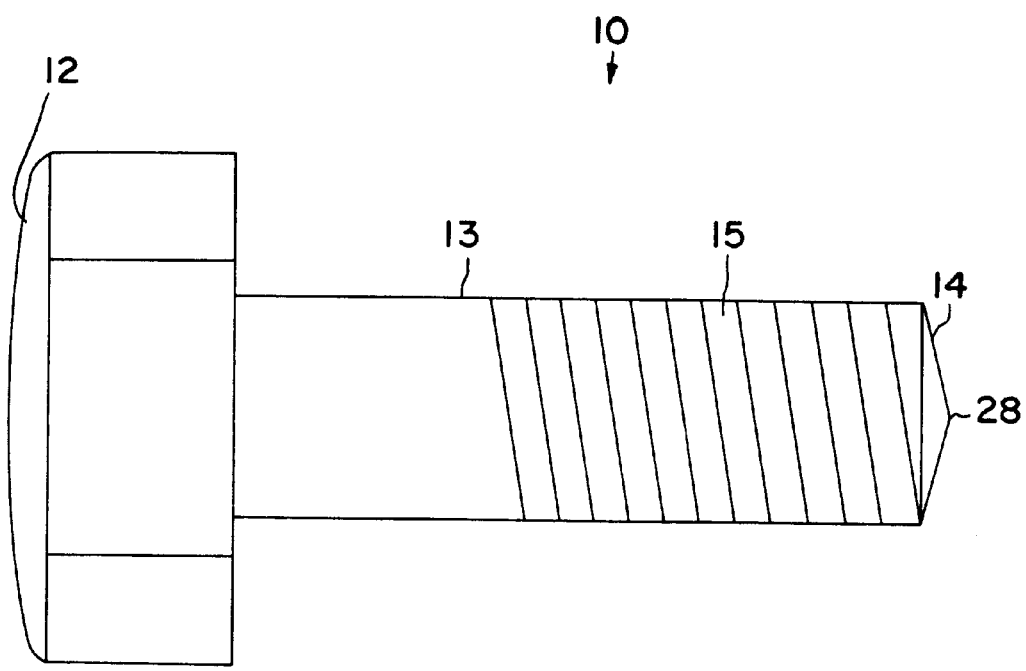
FIG. 16 shows another alternative embodiment of the fastener design according to the present invention in which the fastener has two possible surface contours on its head and end.

Ultrasonic wave inversion through double reflection causes inherent compensation for ultrasonic load measurement errors resulting from bending stresses. FIG. 14 shows fastener 10 with a 90 degree conical point 28 on end 14 which provides a double reflection and wave inversion in such a way that part of the wavefront of ultrasonic wave 16, which propagates down shank 13 of fastener 10 from transducer 18, returns on an axisymmetric parallel path back to transducer 18. Conical point 28 may be, for example, truncated by rounding or flattening the tip thereof as shown in FIG. 14 or may be in the form of a triangle as shown in FIG. 16 and discussed below. Note that 90 degree conical surface 28 provides equal path length across the entire wavefront. As shown in FIG. 14, fastener 10 is not subject to bending.

Figure 15:
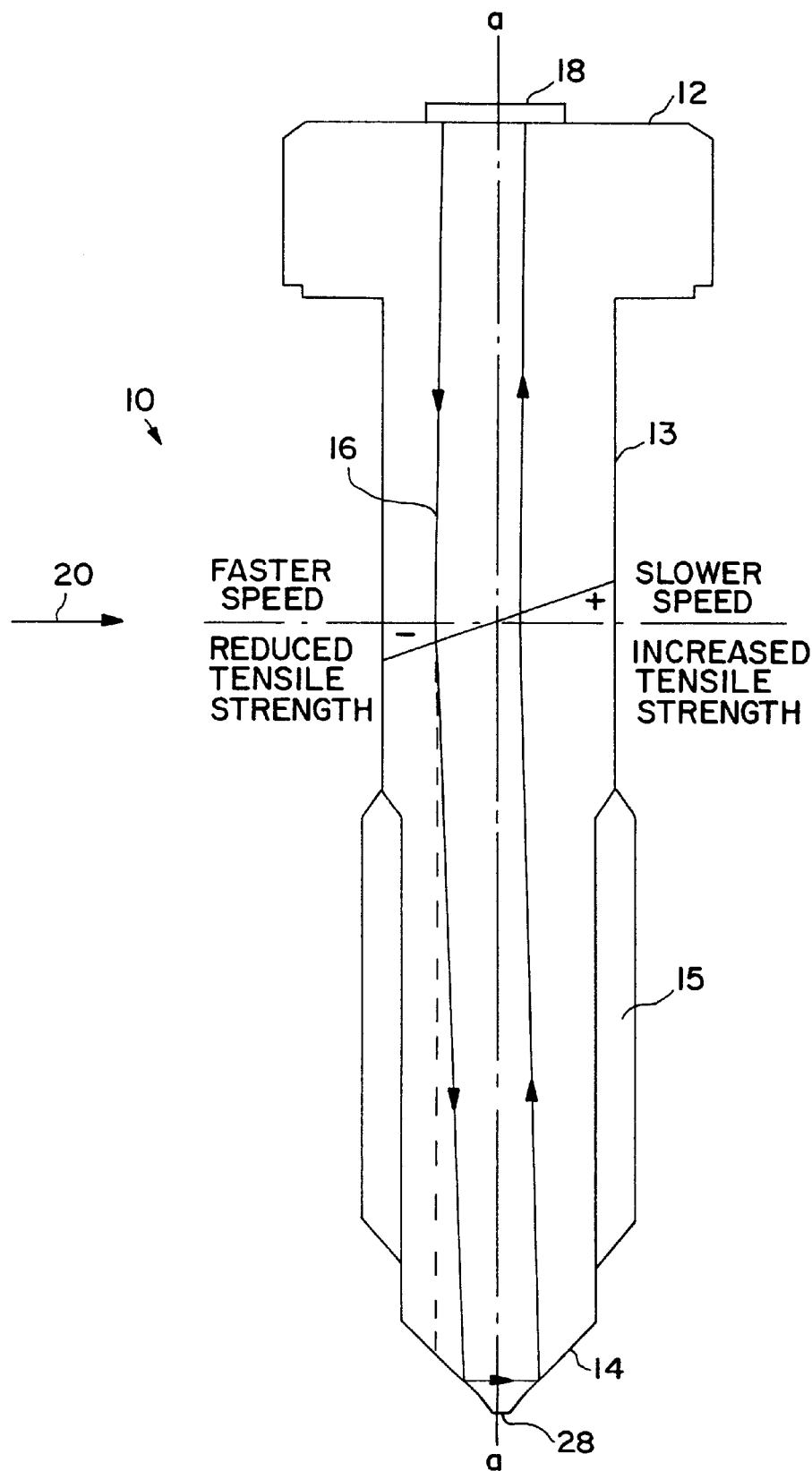
FIG. 15 shows the fastener illustrated in FIG. 14 when subject to bending.

When fastener 10 of the design shown in FIG. 14 is subject to a bending force in the direction of arrow 20, as shown in FIG. 15, the bending force creates an area of reduced tensile stress (indicated by the minus sign) on the left-hand side of fastener 10 and an area of increased tensile stress (indicated by the plus sign) on the right-hand side of fastener 10. Ultrasonic wave 16 is inverted and the wavefront is reflected back on a parallel path (instead of the diverging path with the single flat reflective surface). In addition, phase errors are minimized because each part of the wavefront travels through areas of both positive and negative bending stress because of the axisymmetric inversion.

In FIG. 16, fastener 10 is shown with two possible contours applied to its ends. Specifically, head 12 of fastener 10 has a spherical contour and end 14 of fastener 10 has a conical point 28 which may be optimal in certain cases or which may approximate a certain spherical contour and provide manufacturing advantages. These surface contours preserve the integrity of ultrasonic echoes in the presence of asymmetrical stress.

The bar graph provided below presents the results of tests which were conducted to verify the advantages associated with the model of the present invention. Tests were conducted at 20 MHz using 5 mm diameter thin film transducers of the type described in the prior art. Although all of the bolts used in this test were of the same basic dimensions (M 10×75 mm), the fasteners had five different combinations of head and end surface contours. The average amount of bending required to reach an echo null for each bolt style is shown on the graph. The bolt styles are listed on the y-axis. "Flat-R80" corresponds to a bolt with a flat head and an end with a spherical curvature of 80 mm (80 mm radius of curvature, or "ROC"); "Flat-Flat" corresponds to a bolt with both the head and the end flat (the usual, unmodified condition); "R80-R80" corresponds to a bolt with an 80 mm spherical contour on both the head and the end.

Average Null Position for Bolt Samples With Different Head & End Contour Combinations

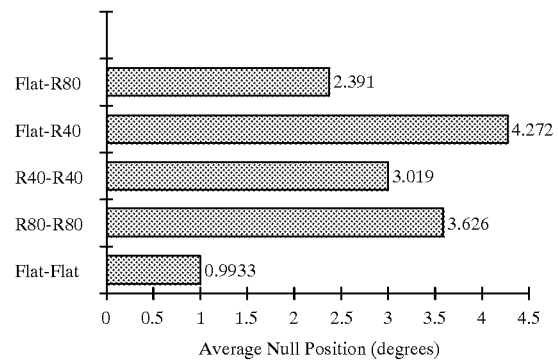

Examination of the graph reveals significant reductions in bending sensitivity when contours are applied to the head and, particularly, to the end of a fastener. In each case a clear increase in null position (a reduction in the sensitivity to bending stresses) is demonstrated over the common "flat-flat" configuration.

Figure 17:
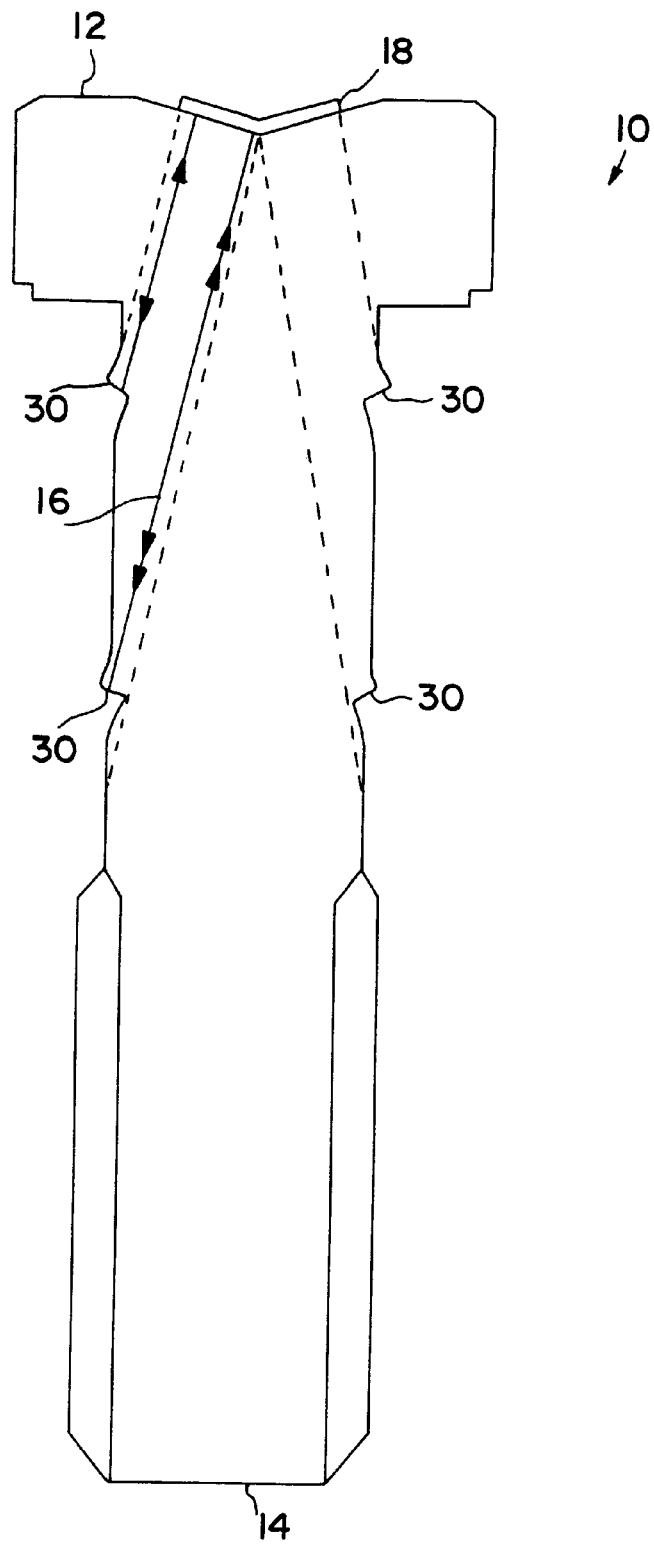
FIG. 17 is a conventional (prior art) fastener with artificial ultrasonic reflectors and a head surface intended to direct sound toward those reflectors.

Contours also may be applied to fasteners in conjunction with existing geometric features such as lightening or internal drive holes. FIG. 17 shows a conventional fastener 10 with artificial ultrasonic reflectors 30. Fastener 10 is used for ultrasonic load measurement. Reflectors 30 are angled such that the ultrasonic wave is reflected from reflector 30 directly back along the same path to transducer 18. When fastener 10 is bent, the ultrasonic wave may be reflected at an angle away from transducer 18. This fastener also exhibits the undesirable effects of the asymmetrical stress gradient from bending.

Figure 18:
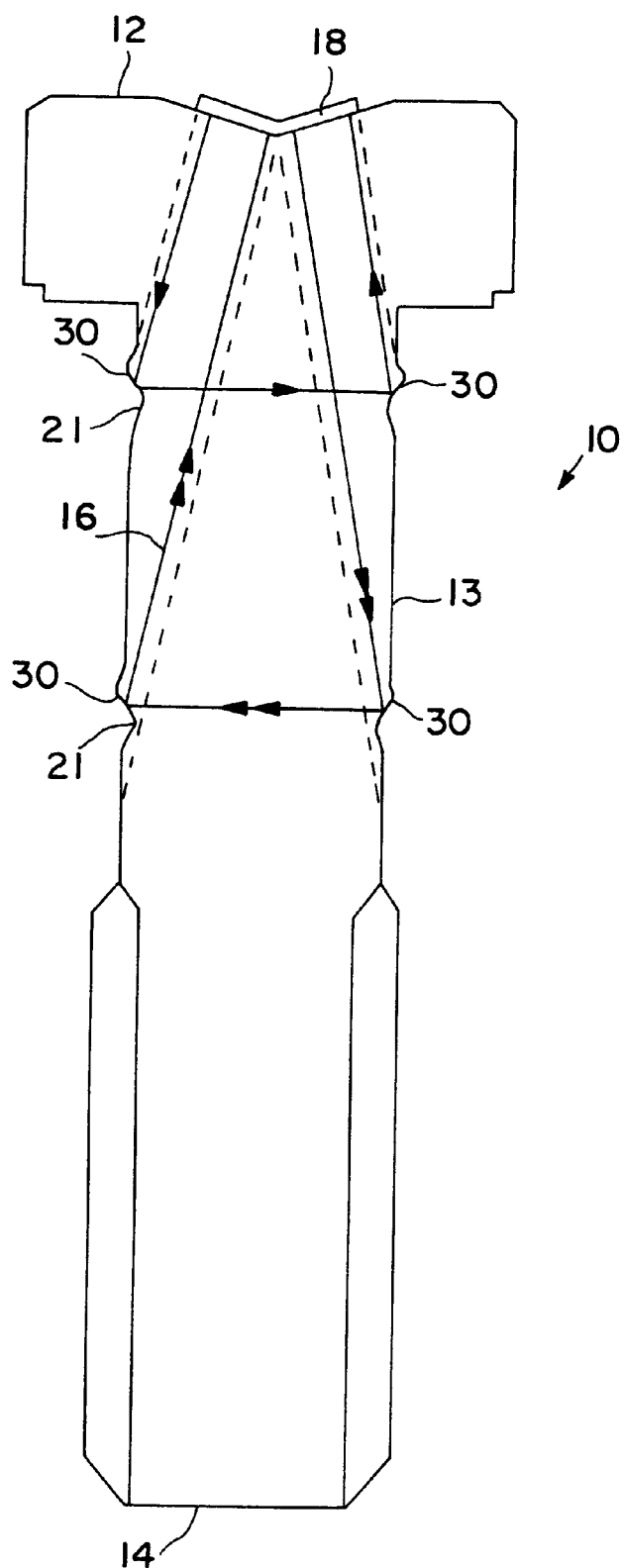
FIG. 18 shows another alternative embodiment of the fastener design according to the present invention in which the fastener has contoured artificial ultrasonic reflectors along with the shank of the fastener, and a conical groove in the head of the fastener.

The design of FIG. 18 is an improvement which incorporates the above concepts of the present invention. In this embodiment, shank 13 of fastener 10 is rolled by conventional metal rolling means to form one or more annular rings 21 reflectors 30, or configured into another shape with a suitable process such that ultrasonic wave 16 is reflected radially across fastener 10 via one reflector 30 to a second reflector 30 and returns via an axisymmetric path which cancels out the undesirable effects of the asymmetrical stress gradient from bending. The two reflectors 30 are angled such that wave 16 is radially reflected across fastener 10. Although head 12 is shown with a conical surface for receiving and transmitting the ultrasonic echoes reflected from reflectors 30, head 12 may be flat or any other shape that will receive and transmit ultrasonic echoes to and from reflectors 30.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, although transducer 18 is illustrated as located on head 12 of fastener 10, transducer 18 could also be placed on end 14 of fastener 10. Also, a laser may be used to transmit ultrasonic waves, and receive ultrasonic echoes, rather than a transducer.

What is claimed:

1. A method of making a load-indicating member comprising the steps of:

providing a load-bearing member subjected to deformation when stressed such that one portion thereof moves relative to another portion thereof, said load-bearing member having a first end, a second end, and a predetermined length;

contouring at least a portion of at least one of said first and second ends of said load-bearing member to reduce the influence of geometric variations and asymmetrical stress in said load-bearing member on ultrasonic measurement, said contour approximating a sphere and having a radius of curvature of approximately 25 to 70 percent of the length of said member; and providing means for transmitting ultrasonic waves through said load-bearing member and receiving ultrasonic echoes, said ultrasonic wave transmitting and receiving means disposed at an end of said load-bearing member.

2. The method according to claim 1, wherein said contour is convex.

3. The method according to claim 1, wherein said contour receives each of said ultrasonic waves directly from said ultrasonic wave transmitting and receiving means and reflects each of said ultrasonic echoes directly back to said ultrasonic wave transmitting and receiving means.

4. A load-indicating device comprising:

a load-bearing member adapted to deform when stressed and having a first end, a second threaded end, and a predetermined length, wherein at least a portion of said second threaded end is contoured to reduce the influence of geometric variations and asymmetrical stress in said load-bearing member on ultrasonic measurement;

wherein said contour is approximately spherical and convex, and has a radius of curvature of approximately 30 to 60 percent of the length of said member; and means for transmitting ultrasonic waves through said load-bearing member and receiving ultrasonic echoes, said ultrasonic wave transmitting and receiving means disposed at said first end of said load-bearing member.

5. The device according to claim 4, wherein said ultrasonic wave transmitting and receiving means is a transducer selected from the group consisting of piezoelectric and electromagnetic transducers.

6. The method according to claim 1, wherein said ultrasonic wave transmitting and receiving means is a transducer selected from the group consisting of piezoelectric and electromagnetic transducers.

7. The method according to claim 1, wherein said ultrasonic wave transmitting and receiving means is a laser.

8. A load-indicating device comprising:

a load-bearing member adapted to deform when stressed and having a first end, a second end, and a predetermined length, wherein at least a portion of at least one of said first and second ends of said load-bearing member is contoured to reduce the influence of geometric variations and asymmetrical stress in said load-bearing member on ultrasonic measurement, said contour approximating a sphere and having a radius of curvature of approximately 25 to 70 percent of the length of said member; and means for transmitting ultrasonic waves through said load-bearing member and receiving ultrasonic echoes, said ultrasonic wave transmitting and receiving means disposed at an end of said load-bearing member.

9. The method according to claim 8, wherein said contour is convex.

10. The device according to claim 8, wherein said contour receives each of said ultrasonic waves directly from said ultrasonic wave transmitting and receiving means and reflects each of said ultrasonic echoes directly back to said ultrasonic wave transmitting and receiving means.

11. The device according to claim 8, wherein said load-bearing member is selected from the group consisting of a fastener, a bolt, a stud and a rivet.

12. The device according to claim 8, wherein said first end of said load bearing member has a recess, said recess having an internal surface and said internal surface is contoured over a portion thereof.

13. The device according to claim 8, wherein said end opposite said contoured end is flat, and said ultrasonic wave transmitting and receiving means is adjacent said flat end.

14. The device according to claim 8, wherein said ultrasonic wave transmitting and receiving means is a transducer selected from the group consisting of piezoelectric and electromagnetic transducers.

15. The device according to claim 14, wherein said selected transducer is permanently attached to one of said first and second ends of said load-bearing member.

16. The device according to claim 14, wherein said selected transducer is removably attached to one of said first and second ends of said load bearing member.

17. The device according to claim 8, wherein said ultrasonic wave transmitting and receiving means is a laser.

18. The device according to claim 8, wherein both said first end and said second end of said load bearing member are contoured.

19. The device according to claim 18, wherein said first end contour has a first radius of curvature and said second end contour has a second radius of curvature, and wherein a sum of said first radius of curvature and said second radius of curvature is approximately equal to the length of said load-bearing member.

20. The device according to claim 18, wherein said first end contour has a radius of curvature of approximately 25 to 70 percent of the length of said member and said second end contour has a radius of curvature of approximately 25 to 70 percent of the length of said member.

21. The device according to claim 13 wherein said contour has a radius of curvature of approximately 30 to 70 percent of the length of said member.

\* \* \* \* \*